(12) United States Patent
McGibbon et al.

(10) Patent No.: US 11,217,114 B2
(45) Date of Patent: *Jan. 4, 2022

(54) SYSTEM AND METHOD FOR NORMALIZING ACTIVITY RESULTS

(71) Applicant: REPerformance Inc., Sudbury (CA)

(72) Inventors: Callen Patrick McGibbon, Sudbury (CA); Milad Mansour, Jr., Sudbury (CA)

(73) Assignee: REPerformance Inc., Sudbury (CA)

( * ) Notice: Subject to any disclaimer, the term of this patent is extended or adjusted under 35 U.S.C. 154(b) by 130 days.

This patent is subject to a terminal disclaimer.

(21) Appl. No.: 16/788,330

(22) Filed: Feb. 12, 2020

(65) Prior Publication Data

US 2020/0258418 A1   Aug. 13, 2020

Related U.S. Application Data

(63) Continuation of application No. 15/190,237, filed on Jun. 23, 2016, now Pat. No. 10,600,333.

(60) Provisional application No. 62/183,416, filed on Jun. 23, 2015.

(51) Int. Cl.
| | | |
|---|---|---|
| G09B 19/00 | (2006.01) | |
| G09B 5/12 | (2006.01) | |
| G16H 20/30 | (2018.01) | |
| G16H 10/60 | (2018.01) | |

(52) U.S. Cl.
CPC ........... *G09B 19/003* (2013.01); *G09B 5/125* (2013.01); *G16H 10/60* (2018.01); *G16H 20/30* (2018.01)

(58) Field of Classification Search
CPC ............ A63B 24/0003; A63B 2220/62; A63B 2220/20; G09B 5/125; G09B 19/003; G16H 10/60; G16H 20/30
USPC ........................................................ 434/247
See application file for complete search history.

(56) References Cited

U.S. PATENT DOCUMENTS

| | | | |
|---|---|---|---|
| 6,571,193 B1 * | 5/2003 | Unuma ................ | A43B 3/0005 340/853.2 |
| 6,746,370 B1 | 6/2004 | Fleming et al. | |
| 7,953,549 B2 * | 5/2011 | Graham ............. | G09B 19/0092 701/466 |
| 10,600,333 B2 | 3/2020 | McGibbon et al. | |
| 2006/0073449 A1 * | 4/2006 | Kumar .................... | F41A 33/00 434/219 |

(Continued)

*Primary Examiner* — Malina D. Blaise
(74) *Attorney, Agent, or Firm* — Bereskin & Parr LLP/S.E.N.C.R.L., s.r.l.

(57) ABSTRACT

A system, method and computer program product for generating normalized activity results. A mobile application is installed on a plurality of computing devices and normalization base data is received for a first user. The first user is assigned to a user population based on the received normalization base data. A comparator population is determined that includes users having normalization base data within a comparator range. Activity results are collected from users in the user population and the comparator population. At least one activity results is received for the user. At least one normalization factor is determined for the user based on the comparator population activity results and the user population activity results. Normalized activity results are determined by adjusting each of the received activity results using the at least one normalization factor. The normalized activity results can then be displayed to the user.

19 Claims, 19 Drawing Sheets

(56) References Cited

U.S. PATENT DOCUMENTS

| | | | |
|---|---|---|---|
| 2007/0185391 A1* | 8/2007 | Morgan | G16H 40/67 600/301 |
| 2007/0232454 A1 | 10/2007 | Kagan et al. | |
| 2008/0033581 A1 | 2/2008 | Doshi et al. | |
| 2008/0090703 A1* | 4/2008 | Rosenberg | A63B 24/00 482/8 |
| 2009/0156908 A1* | 6/2009 | Belalcazar | A61B 5/287 600/301 |
| 2011/0004126 A1* | 1/2011 | Einav | G16H 20/30 600/595 |
| 2011/0230732 A1 | 9/2011 | Edman et al. | |
| 2012/0071733 A1* | 3/2012 | Grey | A61B 5/112 600/301 |
| 2012/0253201 A1* | 10/2012 | Reinhold | H04N 13/254 600/473 |
| 2012/0296455 A1* | 11/2012 | Ohnemus | G16H 10/60 700/91 |
| 2013/0211858 A1* | 8/2013 | Ohnemus | G16H 20/30 705/3 |
| 2014/0073486 A1* | 3/2014 | Ahmed | A61B 5/02427 482/9 |
| 2014/0228985 A1* | 8/2014 | Elliott | A63B 71/06 700/91 |
| 2014/0310013 A1 | 10/2014 | Ram et al. | |
| 2016/0113569 A1* | 4/2016 | Zhao | A61F 5/14 600/300 |
| 2016/0157735 A1* | 6/2016 | Zhang | A61B 5/1112 600/301 |

* cited by examiner

COMPARATOR POPULATION: 30-35 YRS, VIGOROUS ACTIVITY LEVEL

NORMALIZATION ACTIVITY: BENCH PRESS

ACTIVITY LEVEL: 1 (60%)

| LIFESTYLE | AGE | RESULT | NORMALIZED RESULT (AGE) | NORMALIZED RESULT (AGE AND LIFESTYLE) |
|---|---|---|---|---|
| SEDENTARY | 30 | 3 | 3 | 15 |
| | 60 | 2 | 2.4 | 20 |
| LIGHT | 30 | 6 | 6 | 14 |
| | 60 | 5 | 6.5 | 20 |
| MODERATE | 30 | 12 | 12 | 21 |
| | 60 | 9 | 14.4 | 26 |
| VIGOROUS | 30 | 25 | 25 | 25 |
| | 60 | 22 | 31.9 | 31.9 |

FIG. 5

| | COMPARATOR POPULATION: WEIGHTLIFTER | | |
|---|---|---|---|
| | NORMALIZATION ACTIVITY: DEADLIFT | | |
| USER NORMALIZATION BASE DATA | ACTIVITY LEVEL | ACTIVITY RESULT | NORMALIZED RESULT |
| RUNNER, 155LBS | 1 (75%) | 6 | 12 |
| | 2 (100%) | 5 | 12 |
| | 3 (125%) | 1 | 5 |
| | 4 (150%) | 1 | 6 |
| ROWER, 175LBS | 1 (75%) | 16 | 20 |
| | 2 (100%) | 14 | 21 |
| | 3 (125%) | 9 | 15 |
| | 4 (150%) | 4 | 7 |
| CYCLIST, 190LBS | 1 (75%) | 8 | 12 |
| | 2 (100%) | 6 | 10 |
| | 3 (125%) | 4 | 10 |
| | 4 (150%) | 3 | 8 |

FIG. 6

USER POPULATION: RUNNER

| COMPARATOR POPULATION | NORMALIZATION ACTIVITY | ACTIVITY LEVEL | ACTIVITY RESULT | NORMALIZED RESULT |
|---|---|---|---|---|
| CYCLIST | SQUAT | 1 (75%) | 17 | 23 |
| | BENCH PRESS | 1 (60%) | 4 | 5 |
| | LEG PRESS | 1 (75%) | 17 | 22 |
| | DISTANCE RUN | MILE | 6:30 | 7:00 |
| WEIGHTLIFTER | SQUAT | 4 (150%) | 13 | 18 |
| | BENCH PRESS | 4 (120%) | 1 | 7 |
| | DEADLIFT | 4 (150%) | 2 | 8 |
| | DISTANCE RUN | MILE | 6:30 | 8:30 |

FIG. 7

SYSTEM AND METHOD FOR NORMALIZING ACTIVITY RESULTS

CROSS REFERENCE TO RELATED APPLICATIONS

The present application is a Continuation of U.S. patent application Ser. No. 15/190,237, filed on Jun. 23, 2016, which claims the benefit of the filing date of U.S. provisional patent application Ser. No. 62/183,416, filed on Jun. 23, 2015, the disclosures of which are incorporated herein by reference.

FIELD

The described embodiments relate generally to monitoring and tracking activity or fitness results. Specifically, the described embodiments relate to systems and methods for generating normalized activity results.

BACKGROUND

Currently, there are more than 70 million active gym members in North America alone. Many others may be interested in improving their health or fitness, but are not sufficiently motivated to become active. Often, people start a new fitness regime but become disheartened when they don't see immediate results. As a result, some of these people may give up on a fitness regime and return to an inactive lifestyle.

Often, the only tangible feedback people get about their fitness level comes from changes in body weight, or if accessible, body fat measurements. While these indicators may provide some quantitative feedback on fitness level, these measures often cannot account for differences in individual demographic and lifestyle information.

Furthermore, these indicators are strongly tied to appearance. The media bombards us with images and videos of celebrities and athletes who look amazing, but is it reasonable or realistic to ask a working mother or father with children to invest the time and energy needed to look this way? These benchmarks are often unattainable for the average person, and can negatively impact self-esteem. As a consequence, these indicators may prove de-motivational to people who are only beginning to become active or who are trying to increase their frequency or level of activity.

A tool that is able to fairly analyze and compare individual efforts and activity results across varied spectrums of demographics, lifestyles and fitness regimes may provide meaningful feedback and motivation for normal people interested in improving their health and fitness. As well, such a tool may be useful for fitness enthusiasts who are interested in learning how their current results may change if they adjust their lifestyle or fitness regime.

SUMMARY

In some aspects, embodiments described herein provide a method of generating normalized activity results using a server that is in communication with a plurality of computing devices associated with a plurality of users. The method can include providing a mobile application for installation on each of the plurality of computing devices. The method can also include receiving by the mobile application at a first computing device normalization base data for a first user associated with the first computing device, the normalization base data including user base data for at least one normalization dimension and assigning the first user to a user population based on the received normalization base data, where the user population is defined to include users having normalization base data within a user population range for each of the at least one normalization dimensions. The method can also include determining a comparator population for the first user, where the comparator population is defined to include users having normalization base data within a comparator range for each of the at least one normalization dimensions, and for at least one of the normalization dimensions the user population range and the comparator population range do not overlap. The method can further include receiving by the mobile application at the first computing device at least one activity result for the first user and determining at least one normalization factor for the first user based on comparator population activity results received by the server from users in the comparator population and user population activity results received by the server from users in the assigned user population. The method can further include generating normalized activity results for the first user by adjusting each of the at least one activity results using the at least one normalization factor, and displaying the normalized activity results to the user.

In some examples, the method can further include adjusting the at least one normalization factor for the user based on the normalization base data received for the user.

In some examples, the normalization base data for the first user may include user base data for a plurality of normalization dimensions. Determining the at least one normalization factor for the first user can include determining a dimension specific normalization factor for each normalization dimension based on comparator activity results received from users having normalization base data within the comparator population range for that normalization dimension and user population activity results received from users having normalization base data within the user population range for that normalization dimension.

In some examples, the normalization dimensions include at least one of a demographic dimension including demographic user data, a lifestyle dimension including lifestyle user data and a fitness regime dimension including fitness regime user data.

In some examples, the method can further include determining at least one normalization activity for the first user based on the determined comparator population, displaying an indication of the determined at least one normalization activity using the mobile application on the first computing device, and receiving an activity result corresponding to each normalization activity.

In some examples, the method can further include, for one of the normalization activities: determining an activity level based on the normalization base data for the first user, displaying an indication of the determined activity level using the mobile application on the first computing device, and receiving the activity result for that normalization activity by receiving an activity result corresponding to that normalization activity performed at the determined activity level. In some examples, the activity level is determined based on user body weight data included in the received normalization base data for the first user.

In some examples, the at least one normalization factors can include at least one activity-specific normalization factor for each of the at least one normalization activities, and adjusting the activity results received from the first user for each normalization activity can be performed using the activity-specific normalization factors for that normalization activity.

In some examples, the method can further include determining the at least one normalization activity for the user based on the determined comparator population. In some examples, the method can include determining the at least one normalization activity for the user based on the assigned user population.

In some examples, the method can further include automatically detecting the activity results using a user device associated with the user.

In some examples, the method can further include monitoring activity results for the first user over time, and adjusting the normalization base data for the first user based on the monitored activity results.

In some examples, the method can further include collecting by the server normalization base data from the computing devices of a plurality of normalization users from the plurality of users where the normalization base data includes user base data for a plurality of normalization dimensions. The method can also include defining by the server a plurality of normalization populations, each normalization population having a corresponding population base data range and the population base data range for each normalization population corresponds to at least one of the normalization dimensions. The method can also include assigning each normalization user to at least one of the normalization populations, each of the normalization populations to which each normalization user is assigned having a population base data range corresponding to the normalization base data collected for that user, collecting at least one activity result for each of the normalization users using the mobile application installed on the computing device of that normalization user, and defining by the server a plurality of normalization factors by comparing the activity results collected for the different normalization populations, the plurality of normalization factors including the at least one normalization factor determined for the first user.

In some examples, the population base data range for each normalization population corresponds to one of the normalization dimensions.

In some examples, the user population to which the first user is assigned includes a first plurality of normalization populations, one normalization population for each normalization dimensions. The comparator population can include a second plurality of normalization populations, one normalization population for each normalization dimension, where the second plurality of normalization populations is different from the first plurality of normalization populations, and the at least one normalization factor is determined for the first user by comparing the activity results for the first plurality of normalization populations with the activity results for the second plurality of normalization populations.

In some examples, the method can further include monitoring by the server activity results collected from each of the normalization users over time using the mobile application, and re-defining, by the server, at least one of the normalization factors based on the monitored activity results.

In some examples, the method can further include monitoring, by the server, activity results from each of the normalization users over time collected using the mobile application, updating the normalization base data for a particular normalization user based on the monitored activity results for that normalization user, and removing the particular normalization user from one of the normalization populations to which that user was assigned and re-assigning that particular normalization user to a different normalization population based on the updated normalization base data.

In some aspects, embodiments described herein provide a system for generating normalized activity results for a first user. The system can include a plurality of computing devices associated with a plurality of users and a server in communication with the plurality of computing devices. The server can be configured to provide a mobile application for installation on each of the plurality of computing devices. A first computing device from the plurality of computing devices associated with the first user can be configured by the mobile application to receive normalization base data for the first user, the normalization base data include user base data for at least one normalization dimension; assign the first user to a user population based on the received normalization base data, the user population being defined to include users having normalization base data within a user population range for each of the at least one normalization dimensions; and determine a comparator population for the first user, the comparator population being defined to include users having normalization base data within a comparator range for each of the at least one normalization dimensions, wherein for at least one of the normalization dimensions the user population range and the comparator population range do not overlap. The server can also be configured to collect, using the mobile application, comparator population activity results from a plurality of comparator users for whom the normalization base data includes user base data for the at least one normalization dimension within the comparator population range for that normalization dimension; collect, using the mobile application, user population activity results from a plurality of users for whom the normalization base data includes user base data for the at least one normalization dimension within the user population range for that normalization dimension; and define at least one normalization factor for the comparator population and the user population using the comparator population activity results and the user population activity results. The first computing device can be further configured by the mobile application to determine the at least one normalization factor for the first user based on the comparator population and the normalization base data received for the user; receive at least one activity result for the first user; generate normalized activity results for the first user by adjusting each of the at least one activity results using the at least one normalization factor; and display the normalized activity results.

In some examples, at least one of the normalization factors determined for the user can be adjusted based on the normalization base data received for the user.

In some examples, the normalization base data for the first user includes user base data for a plurality of normalization dimensions, and the server can be configured to determine the at least one normalization factor by determining a dimension specific normalization factor for each normalization dimension based on comparator activity results received from users having normalization base data within the comparator population range for that normalization dimension and user population activity results received from users having normalization base data within the user population range for that normalization dimension.

In some examples, the normalization dimensions include at least one of a demographic dimension comprising demographic user data, a lifestyle dimension comprising lifestyle user data and a fitness regime dimension comprising fitness regime user data.

In some examples, the first computing device can be further configured by the mobile application to determine at least one normalization activity for the first user based on the determined comparator population, display an indication of the determined at least one normalization activity; and receive at least one activity result corresponding to each determined normalization activity.

In some examples, the first computing device can be further configured by the mobile application to determine an activity level for one of the normalization activities based on the normalization base data for the user, display an indication of the determined activity level, and receive an activity result corresponding to that normalization activity at the determined activity level.

In some examples, the first computing device can be further configured by the mobile application to determine the activity level based on user body weight data included in the received normalization base data for the first user.

In some examples, the server can be configured to define the at least one normalization factor to include at least one activity-specific normalization factor for each of the at least one normalization activities, and the first computing device can be configured by the mobile application to adjust the activity results received from the first user for each normalization activity using the activity-specific normalization factors for that normalization activity.

In some examples, the first computing device can be further configured by the mobile application to determine the at least one normalization activity for the user based on the determined comparator population. In some examples, the first computing device can be further configured by the mobile application to determine the at least one normalization activity for the user based on the assigned user population.

In some examples, the system may also include an activity tracking device associated with the first computing device and the activity tracking device can be configured to automatically detect the at least one activity result.

In some examples, the first computing device can be further configured by the mobile application to monitor activity results for the first user over time, and adjust the normalization base data for the first user based on the monitored activity results.

In some examples, the server can be further configured to collect normalization base data for a plurality of normalization users, the normalization base data including user base data for a plurality of normalization dimensions; define a plurality of normalization populations, each normalization population having a corresponding population base data range and the population base data range for each normalization population corresponds to one of the normalization dimensions, assign each normalization user to at least one of the normalization population, each of the normalization populations to which each normalization user is assigned having a population base data range corresponding to the normalization base data collected for that user, collect at least one activity result for each of the normalization users using the mobile application, and define the plurality of normalization factors by comparing the activity results collected for the different normalization populations the plurality of normalization factors including the at least one normalization factor determined for the first user.

In some examples, the population base data range for each normalization population corresponds to one of the normalization dimensions.

In some examples, the user population to which the first user is assigned includes a first plurality of normalization populations, one normalization population for each normalization dimension. The comparator population can include a second plurality of normalization populations, one normalization population for each normalization dimension, where the second plurality of normalization populations is different from the first plurality of normalization populations. The server can be configured to define the at least one normalization factor for the first user by comparing the activity results for the first plurality of normalization populations with the activity results for the second plurality of normalization populations.

In some examples, the server can be further configured to monitor activity results collected from each of the normalization users over time using the mobile application, and re-define at least one of the normalization factors based on the monitored activity results.

In some examples, the server can be further configured to monitor activity results for each of the normalization users over time using the mobile application, update the normalization base data for a particular normalization user based on the monitored activity results for that normalization user, and remove the particular normalization user from one of the normalization populations to which that user was assigned and re-assign that particular normalization user to a different normalization population based on the updated normalization base data.

In some aspects, embodiments described herein provide a non-transitory, computer-readable storage medium storing instructions executable by a processor coupled to the storage medium, the instructions for programming the processor to receive normalization base data for a first user, the normalization base data including user base data for at least one normalization dimension; assign the first user to a user population based on the received normalization base data, the user population being defined to include users having normalization base data within a user population range for each of the at least one normalization dimensions; determine a comparator population for the first user, where the comparator population is defined to include users having normalization base data within a comparator range for each of the at least one normalization dimensions, where for at least one of the normalization dimensions the user population range and the comparator population range do not overlap; receive at least one activity result for the first user; determine at least one normalization factor for the first user, the at least one normalization factor defined using comparator population activity results collected from a plurality of comparator users for whom the normalization base data includes user base data for the at least one normalization dimension within the comparator population range for that normalization dimension and user population activity results collected from a plurality of users for whom the normalization base data includes user base data for the at least one normalization dimension within the user population range for that normalization dimension; generate normalized activity results for the first user by adjusting each of the at least one activity results using the at least one normalization factor; and display the normalized activity results.

BRIEF DESCRIPTION OF THE DRAWINGS

A preferred embodiment of the present invention will now be described in detail with reference to the drawings, in which:

FIG. 5 shows a diagram illustrating an example table of activity results and normalized activity results for users in various example user populations;

FIG. 6 shows a diagram illustrating another example table of activity results and normalized activity results for users in various example user populations;

FIG. 7 shows a diagram illustrating an example table of activity results for a user and normalized activity results for the user with different example comparator populations;

DESCRIPTION OF EXEMPLARY EMBODIMENTS

Figure 1:
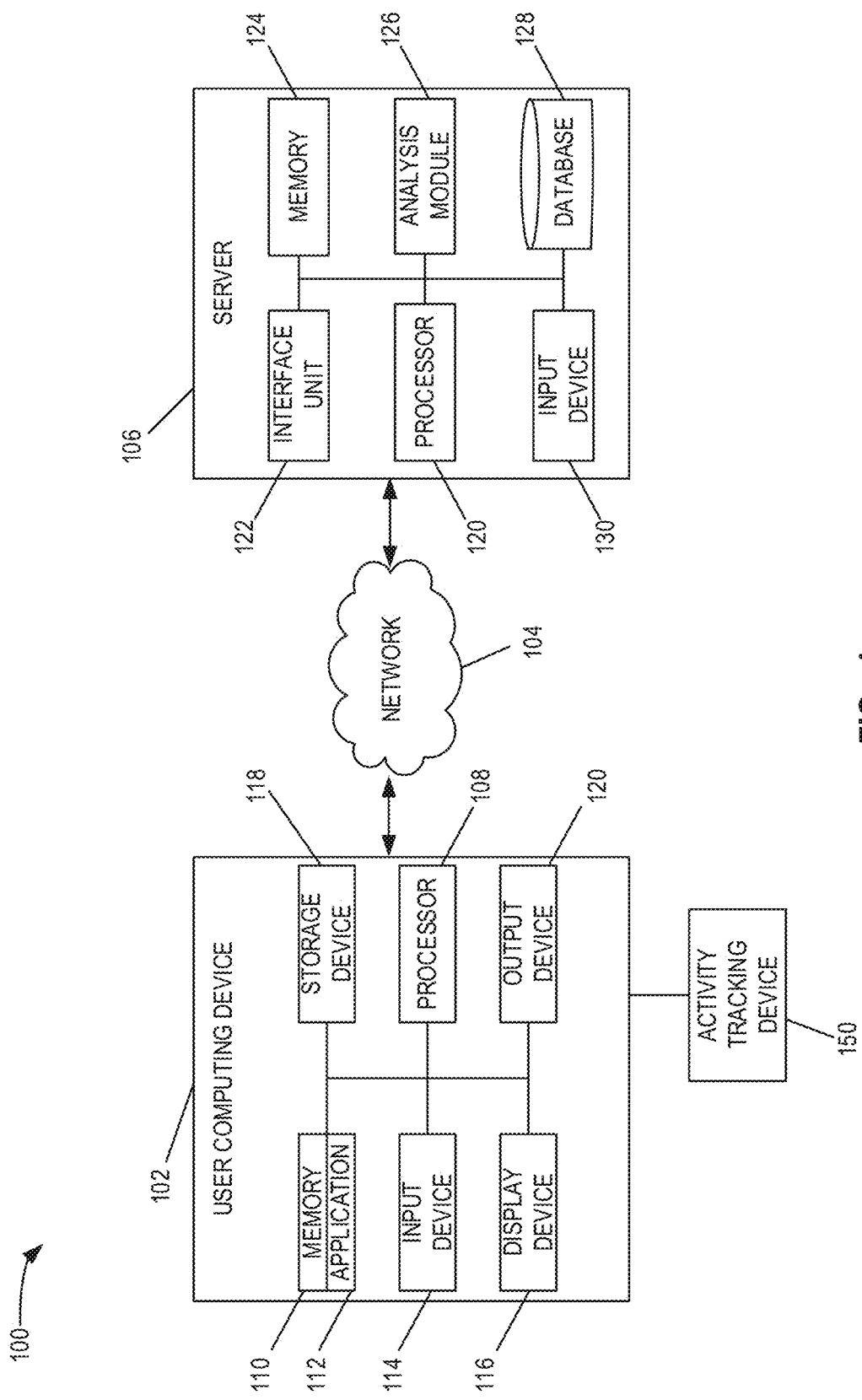
FIG. 1 shows a block diagram of an example embodiment of a system for generating normalized activity results.

Various systems or methods will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" may be used to indicate that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are example embodiments of systems, methods, and computer program products for generating normalized activity results for a user. The systems and methods described herein can be used compare, track, analyze and motivate personal fitness results. Embodiments of the systems and methods described herein allow users to compare, rank and normalize activity results with others in the fitness community or in the population at large. The teachings herein allow a user's activity results to be normalized to indicate how their actual results would change or translate if their demographics, lifestyle or fitness regime were different.

In general, the system provides a mobile application to a user for installation on a user computing device. The mobile application can prompt collection of normalization base data from the user using a series user interfaces. The normalization base data can then be stored on the user device by the mobile application and/or may be provided to a server in communication with the user device.

The normalization base data may include demographic data such as the user's age, sex, height, weight, location, race, ethnicity and the like. The normalization base data may also include lifestyle data such as exercise frequency, exercise intensity/exertion level, nutrition level, sleep patterns, and the like. The normalization base data may also include fitness regime data indicating the user's specific fitness regime such as activity types and exercise regime duration.

A user's normalization base data, or a portion thereof, may also be collected automatically in embodiments described herein. For example, the user's weight may be collected using a communicative coupling between a user device and an electronic scale used by the user. Other aspects of the normalization base data, such as exercise frequency, exercise intensity, activity types, and exercise regime duration for example, may also be collected or modified using activity tracking devices communicatively coupled to the user's device. In some cases, the user's device may also function as the activity tracking device. This may enable the system to account for inaccuracies in the user's self-reported normalization base data or changes in the normalization base data over time.

The fitness regime data may identify the user as a member of a particular fitness regime population such as a cyclist, weightlifter, runner, or swimmer for example. In some embodiments, the fitness regime populations (and user populations in general) can be defined in various ways, e.g. with more or less specificity, or different population ranges, based on the normalization base data collected from a plurality of normalization users. For example, user populations may be defined by identifying clusters of users with similar normalization base data.

The systems and methods described herein allow users to normalize their activity results to compare their activity results with users having different demographic information (e.g. age or gender or weight), different lifestyle data (e.g. nutrition levels, general activity frequency such sedentary or moderately active, sleep time), or different fitness regimes (e.g. cyclists, rowers, swimmers, weightlifters). Generating normalized activity results may allow users to fairly compare their own activity results with other users across all spectrums of health, lifestyles, demographics, and fitness regimes.

For example, the normalized fitness results may allow users who are active on average twice a week to compare normalized activity results with users who are active on average 5 times a week. The normalized activity results generated may motivate users to adjust their lifestyle or fitness regime by displaying results those users may achieve with their current level of effort if they adjust their lifestyle or fitness regime. Furthermore, the systems and methods allow users from different demographic groups to compare results. For example, older users may be able to train with younger users such as children and grandchildren in a safe and motivating environment.

To determine the normalized activity results, a comparator population can be determined for the user. The comparator population defines normalization base data within a comparator range. For example, a comparator range may cover normalization base data for ages 20-25, male, 6'0-6'2, with exercise frequency of 5+ times weekly. This comparator range may be used to generate normalized activity results for the user that indicate results that may be achieved if the user changed their lifestyle to exercise 5+ times weekly and their demographic data was adjusted to correspond to a 20-25 year old male with a height between 6'0-6'2.

Another example of a comparator population comparator range could cover normalization base data with weightlifting activity types, with a moderate exercise frequency, with exercise regime duration of 3+ months. This example comparator range may be used to normalize activity results for the user to determine how their results (i.e. effort or exertion) may translate if they were to adjust their fitness regime to a moderate weightlifting fitness regime.

In some cases, the comparator population can be automatically selected for the user. For example, the system may automatically select a comparator population that represents more rigorous or more active normalization base data. In some embodiments, the user may provide fitness goal information to the system. The system may automatically select a comparator population based on the user's fitness goals. This may provide motivation to the user to adjust their fitness regime to achieve the results from the comparator population. For example, if the user indicates that athletic performance in a specific sport, say cycling, is a fitness goal, the comparator population may be chosen to have a comparator range including normalization base data identified to correspond to cyclists.

In some cases, the user may select a comparator population. For example, the user may select a comparator population with a comparator range that includes the normalization based data of another user to whom they wish to be compared. For example, a moderately active child may wish to motivate their older parent who is currently sedentary (or vice versa) to become more active. To do so, one or both of the users may each select a comparator population with a comparator range of normalization base data that reflects the other user to whom they wish to be compared. This allows the users to exercise together and compare results fairly even though they have different fitness and health baselines. Using normalized fitness results may allow such users to motivate themselves or each other in the form of friendly competition.

In some cases, a user may select a comparator population when considering whether to adjust their fitness regime. For example, a user may be considering whether to take up cycling or weightlifting, or considering whether to adjust to a moderate exercise regime or a rigorous exercise regime for example. The user may select a first comparator population with a comparator range of normalization base data that includes a cycling fitness regime to see how their activity results are normalized when compared to the first comparator population. The user may then select a second comparator population with a comparator range with normalization base data including a weightlifting fitness regime and see how their activity results are normalized when using the second comparator population. The user may then make a more informed decision about whether to take up cycling or weightlifting. The user's fitness regime may then be adjusted based on the normalized activity results. In some cases, the mobile application installed on the user's device may prompt fitness regime suggestions for the user based on fitness goals, and then allow the user to generate normalized activity results using a comparing population for the suggested fitness regime to provide additional guidance to the user.

In general, at least one activity result can be received for the user. Each activity result may correspond to a normalization activity performed by the user. There can be various different types and examples of normalization activities. In some cases, a plurality of activity results may be received for a particular normalization activity for the user. In some cases, the plurality of activity results received for the user for a particular normalization activity may be averaged prior to being normalized.

The system can determine at least one normalization factor for the user. The normalization factors can be determined based on the comparator population determined for the user and the user's normalization base data. For example, the user may be assigned to a user population. The user population has a user population range of normalization base data. The user can be assigned to a particular user population if the user's normalization base data falls within the user population range for that particular user population. The normalization factors may be determined for the user based on the user population and the comparator population.

For example, the system may collect activity results for the normalization activities for a first plurality of users falling into the user population and a second plurality of users falling into the comparator population. The system may then correlate the results for the two populations to determine the normalization factors.

In some cases, the normalization base data may include a plurality of normalization dimensions. For instance, the normalization dimensions may include one or more demographic data dimensions, one or more lifestyle data dimensions, and/or one or more fitness regime data dimensions. In some cases, the user population and/or comparator population may include a plurality of normalization populations. For instance, the user population and/or comparator population may include one normalization population for each dimension. In some cases, the normalization factors determined between the user population and the comparator population may include one normalization factor for each normalization dimension. The normalization factors for each dimension can be used to adjust the user's activity results to generate the normalized activity results.

For example, the user may be assigned to a user population with a user population range that includes normalization base data in four normalization dimensions ages 40-45, height 6'0-6'2, weight 200-220 lbs, and a moderate exercise frequency. In this example, the user population may include 4 normalization populations, one for each normalization dimension. Similarly, the comparator population may also include four normalization dimensions, and the comparator range in at least one of the normalization dimensions is different from the user population range. For example, the comparator population may have a comparator range including height 6'0-6'2 and weight 200-220 lbs, but ages 45-50 and a vigorous (i.e. frequent) exercise frequency. The user here might want to understand how their activity results may change as they get older if they increase their exercise frequency.

In some embodiments, the system may determine only one normalization factor, comparing the user population to the comparator population overall. However, in some cases, the system may determine one normalization factor for each normalization dimension. In the example given above, the system may determine two normalization factors, one each for the age dimension and the exercise frequency dimension.

As well, the normalization factors determined for the user may be dependent on the normalization activity performed by the user. For example, different normalization factors may be determined when activity results for a squat normalization activity are normalized between a cycling user population and a weightlifting user population than when activity results for a distance run normalization activity are normalized.

In some cases, the normalized activity results for a user may be generated based on user-specific body weight data for the user. For example, a normalization factor for each normalization activity (or activity level) may be determined based on the body weight data included in the user's normalization base data. Alternatively, in some embodiments a user-specific activity level may be selected for each user based on the body weight data for that user and the activity level. Thus, users with different body weight data may be prompted to perform the same normalization activity at different user-specific activity levels. The user-specific activity level may effectively normalize users' results in the weight dimension for an activity level without adjusting their actual activity results using a normalization factor based on the weight dimension.

User-specific activity levels allow users with different body weight data to perform the same normalization activity at effectively equivalent activity levels (for their weight), while the user-specific activity level for each user may be different. In some such cases, the activity results collected using user-specific activity levels corresponding to the same activity level may be correlated to one another or considered substantially equivalent (at least in the weight dimension). For example, users may perform activities involving weights with user-specific weight levels selected as a percentage of the user's body weight data. The activity level may be determined as the same percentage for each user, but the user-specific activity level, i.e. the weight at which the activity was actually performed, can differ. In some embodiments, each user may have a different user-specific activity level, but the activity results may be associated with the same activity level for each user.

In some cases, the activity level may be determined based on a fitness category determined by the mobile application as a fitness category to be assessed. For example, the user may select a particular fitness category that they wish to assess. The normalization factors determined for the user may depend on the activity level and/or a corresponding fitness category chosen. For example, the user's stamina may not be expected to decrease as rapidly with age as the user's power. Accordingly, normalization activities performed at an activity level corresponding to the stamina fitness category may use different normalization factors than normalization activities performed at an activity level corresponding to the power fitness category.

In some cases, for example, the normalization factors for a normalization dimension and fitness category may be determined as a scale or spectrum. For example, normalization factors for the age dimension and strength fitness category may be determined using a strength-age normalization plot. The strength-age normalization plot may identify a peak age or peak age range. The peak age or peak age range may indicate the age at which a user's strength typically peaks, based on collected activity results. For example, the peak age or peak age range may be about 30 years of age or a range of about 20-40 years of age.

The strength-age normalization plot may have a slope or series of plot points for all other ages that can be determined as a function or percentage of the peak age strength. For example, the strength-age normalization plot may indicate that after the peak age or peak age range, the normalization factor determined for a user may decline at a defined rate each year. For example, the defined rate of decline may be about 1%+/−0.05% per year. In such cases, the normalization factor for the age dimension may be function of the user's age, the comparator age range, and the user's activity results. For example, the normalized activity results may be determined according to:

$$NAR = \frac{AR}{USR \times CSR}$$

where NAR=normalized activity results, AR=activity results, USR=average user population strength (e.g. as a function/percentage of peak strength), CSR=average comparator population strength (e.g. as a function/percentage of peak strength). Normalization factors for other fitness categories and/or other normalization dimensions may be determined in a similar manner.

The example embodiments of the systems and methods described herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a pushbutton keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level computer programming language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Referring now to FIG. 1, shown therein is block diagram illustrating an example embodiment of a system 100. The system 100 is provided as an example and there can be other embodiments of the system 100 with different components or a different configuration of the components described herein. The system 100 further includes several power supplies (not all shown) connected to various components of the system 100 for providing power thereto as is commonly known to those skilled in the art.

System 100 includes a user computing device 102 which communicates with a server 106 via a network 104. Many components of user device 102 and/or server 106 may be implemented using a server computer, desktop computer, notebook computer, tablet, PDA, smartphone, or another computing device such as a "smart" device that may be networked through the "Internet of Things". User device 102 and server 106 can include a connection with the network 104 such as a wired or wireless connection to the Internet. In some cases, network 104 may include other types of computer or telecommunication networks.

User device 102 may include one or more of a processor 108, a memory 110, an input device 114, a display device 116, an output device 120, and a secondary storage device 118.

The processor 108 controls the operation of the user device 102 and can be any suitable processor, controller or digital signal processor that can provide sufficient processing power processor depending on the configuration, purposes and requirements of the user device 102 as is known by those skilled in the art. For example, the processor 108 may be a high performance general processor. In alternative embodiments, the processor 108 may include more than one processor with each processor being configured to perform different dedicated tasks. In alternative embodiments, specialized hardware can be used to provide some of the functions provided by the processor 108.

Memory 110 may include random access memory (RAM) or similar types of memory. Also, memory 110 may store one or more applications 112 for execution by processor 108. Applications 112 may correspond to software modules comprising computer executable instructions to perform processing for the functions described below. For example, a fitness normalization application may be installed on the user device 102. The fitness normalization application may be provided to the user device 102 by the server 106, e.g. through an app store. References to acts or functions by the user device 102 imply that processor 108 is executing computer-executable instructions (e.g., a software program such as a fitness normalization application) stored in memory 110.

Secondary storage device 118 may include a hard disk drive, floppy disk drive, CD drive, DVD drive, Blu-ray drive, or other types of non-volatile data storage. Processor 108 may execute applications, computer readable instructions or programs. The applications, computer readable instructions or programs may be stored in memory 110 or in secondary storage 118, or may be received from the Internet or other network 104.

Input device 114 may include any device for entering information into device 102. For example, input device 114 may be a keyboard, key pad, cursor-control device, touchscreen, camera, or microphone. In some cases, some of these components can be integrated with one another.

Display device 116 may include any type of device for presenting visual information. For instance, the display 116 may be a cathode ray tube, a flat-screen monitor and the like if the user device 102 is a desktop computer. In other cases, the display 116 may be a display suitable for a laptop, tablet or handheld device such as an LCD-based display and the like. In some embodiments, the display 116 may be used to display information and user interface screens to a user such as the examples user interfaces shown in FIGS. 9-19. The user interface screens may be used to prompt collection of normalization base data, activity results and to display normalization activities, normalized activity results and suggested fitness regimes among other things.

Output device 120 may include any type of device for presenting a hard copy of information, such as a printer for example. Output device 120 may also include other types of output devices such as speakers, for example. In some cases, device 102 may include multiple of any one or more of processors, applications, software modules, second storage devices, network connections, input devices, output devices, and display devices.

The server 106 may include a processor 120, and interface unit 122, memory 124, analysis module 126, and one or more databases 128. Processor 120 and memory 124 can be similar to processor 108 and memory 110.

The interface unit 122 may be any interface that allows the server 106 to communicate with other devices or computers. In some cases, the interface unit 122 may include at least one of a serial port, a parallel port or a USB port that provides USB connectivity. The interface unit 122 may also include at least one of an Internet, Local Area Network (LAN), Ethernet, Firewire, modem or digital subscriber line connection. Various combinations of these elements may be incorporated within the interface unit 122.

Analysis module 126 is an example of an application that may be implemented by processor 120. Analysis module 126 can be used to monitor and analyze activity results for one or more normalization users and generate normalization factors based on the monitored activity results and analysis thereof. The analysis module 126 may operate in conjunction with a fitness normalization application installed on the user device 102.

Database 128 may be similar to storage device 118. Database 128 may be used to store normalization base data and activity results for a plurality of users. Database 128 may also be used to store various normalization populations and associated activity results, as well as normalization factors defined for various different user populations and comparator populations.

In some cases, the user device 102 and/or the server 106 may include a wireless unit such as a radio that communicates utilizing CDMA, GSM, GPRS or Bluetooth protocol according to standards such as IEEE 802.11a, 802.11b, 802.11g, or 802.11n. The wireless unit can be used to communicate with other devices or computers.

In some cases, the user device 102 can be coupled to an activity tracking device 150. Activity tracking device 150 can be any type of device used to collect activity results for the user associated with user device 102. For example, activity tracking device 150 may be a data gathering component associated with exercise equipment such as a treadmill or a stationary bike.

Activity tracking device 150 can also be a fitness monitoring device and/or application such as a heart rate monitor, cadence monitoring device, or other fitness tracking device.

For example, the activity tracking device 150 may use an inertial motion sensor such as a three-dimensional accelerometer to automatically track the user's movements. In some cases, the activity tracking device 150 may automatically detect activity results for the user and provide the detected activity results to the user device 102.

In some cases, activity tracking device 150 can be integrated with user device 102. For example, a fitness monitoring and/or tracking application may be installed on user device 102. The fitness tracking application may be incorporated into the fitness normalization application or may be separate. The fitness tracking application may automatically track activity results for a user, for example after receiving an indication of a normalization activity being performed.

Activity tracking device 150 may also monitor the user's to update or refine the normalization base data for the user. For example, activity tracking device 150 may identify that the user's activity level or exertion level is different from the information provided by the user. The activity tracking device 150 may automatically update the normalization data stored for the user to provide more accurate normalization factors for the user, and to more accurately track the activity results associated with the user.

Although device 102 and server 106 are depicted with various components, one skilled in the art will appreciate that this device may in some cases contain fewer, additional or different components. In addition, although aspects of an implementation of device 102 or server 106 may be described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM. The computer-readable media may include instructions for controlling device 102, server 106 and/or processors 108 and 120 to perform a particular method.

In the description that follows devices such as user device 102 and server 106 are described performing certain acts. It will be appreciated that any one or more of these devices may perform an act automatically or in response to an interaction by a user of that device. That is, the user of the device 102 may manipulate one or more input devices 114 (e.g. a touchscreen, a mouse, or a button) causing the device 102 to perform the described act. In many cases, this aspect may not be described below, but it will be understood.

In some embodiments, at least some portions of the systems and methods described herein may be implemented on the user device 102 operating under the control of a fitness normalization application. In some cases, the operations of the fitness normalization application may be distributed between the user device 102 and the server 106. For example, the user device 102 may be used to gather normalization base data and activity results for the user. The server 106 may store normalization base data and activity results from a plurality of user in databases 128. The server 128 may use this information to define a plurality of normalization factors, and update the normalization factors as further results are gathered over time.

Various other features of the systems and methods described herein could be performed by either the user device 102 or the server 106 in different embodiments. For instance, the normalization factors for a particular user may be determined either on the user device 102 (e.g. if the normalization factors for the user's user population and the comparator population are stored on the device) or on the server 106. In some cases, it may be preferable for the normalization factors to be determined for a user by the server 106, at least initially, to reduce the storage requirements for user device 102.

In some cases, the normalization factors can be stored on database 128. After receiving initial normalization base data for the user, the user device 102 may request one or more normalization factors from the server 106. In some cases, the server 106 may transmit only the normalization factors for the particular comparator population and the current normalization base data to the user device 102 to minimize storage requirements on the user device 102. In other cases, once the normalization base data has been collected for a user, the server 106 may send all relevant normalization factors (based on the normalization base data), or the most frequently requested normalization factors to user device 102. This allows user device 102 to still provide some normalization functions even when user device 102 is unable to communicate with the server 106.

Figure 2:
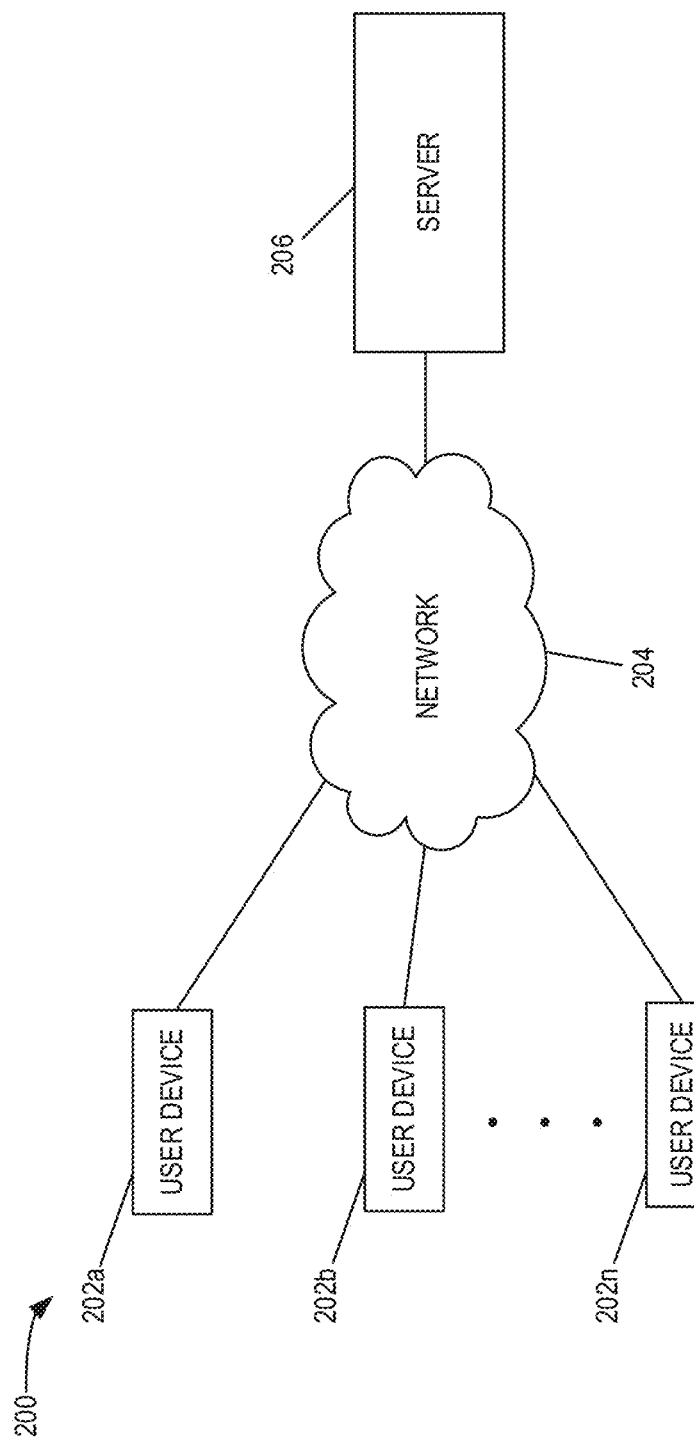
FIG. 2 shows a block diagram of another example embodiment of a system for generating normalized activity results.

Referring now to FIG. 2, shown therein is a block diagram of a system 200 for generating normalized activity results. System 200 includes a plurality of users devices 202a-202n configured to communicate with a server 206 via a network 204. In general, user devices 202 may be similar to user device 102, server 206 may be similar to server 106 and network 204 may be similar to network 104.

System 200 is an example of a system that can be used to generate and refine normalization factors. System 200 can be used to track and monitor activity results from a plurality of normalization users over time. Server 206 can store the normalization base data for the normalization users associated with the user devices 202. Over time, activity results can be collected at user devices 202. These activity results can be transmitted to server 206 via network 204. The server 206 can store these activity results in association with the normalization base data for each normalization user.

Furthermore, server 206 can analyze the stored activity results and normalization base data to generate normalization factors. The normalization base data for each normalization user can be used to assign that normalization user to a normalization population. The activity results collected for that normalization user can then be associated with the normalization population along with the activity results collected from other normalization users assigned to that normalization population.

Average activity results can be identified for each of the normalization populations. Normalization factors between a pair of normalization populations can then be determined by comparing the average activity results for each of the normalization populations. In some cases, each normalization population may correspond to a single normalization dimensions. As a result, a normalization user may be assigned to a plurality of normalization populations, one for each normalization dimension. The collected activity results for that user can then be associated with each of the normalization populations to which that user was assigned. Normalization factors can then be determined for each of the normalization populations in each normalization dimension.

Figure 3:
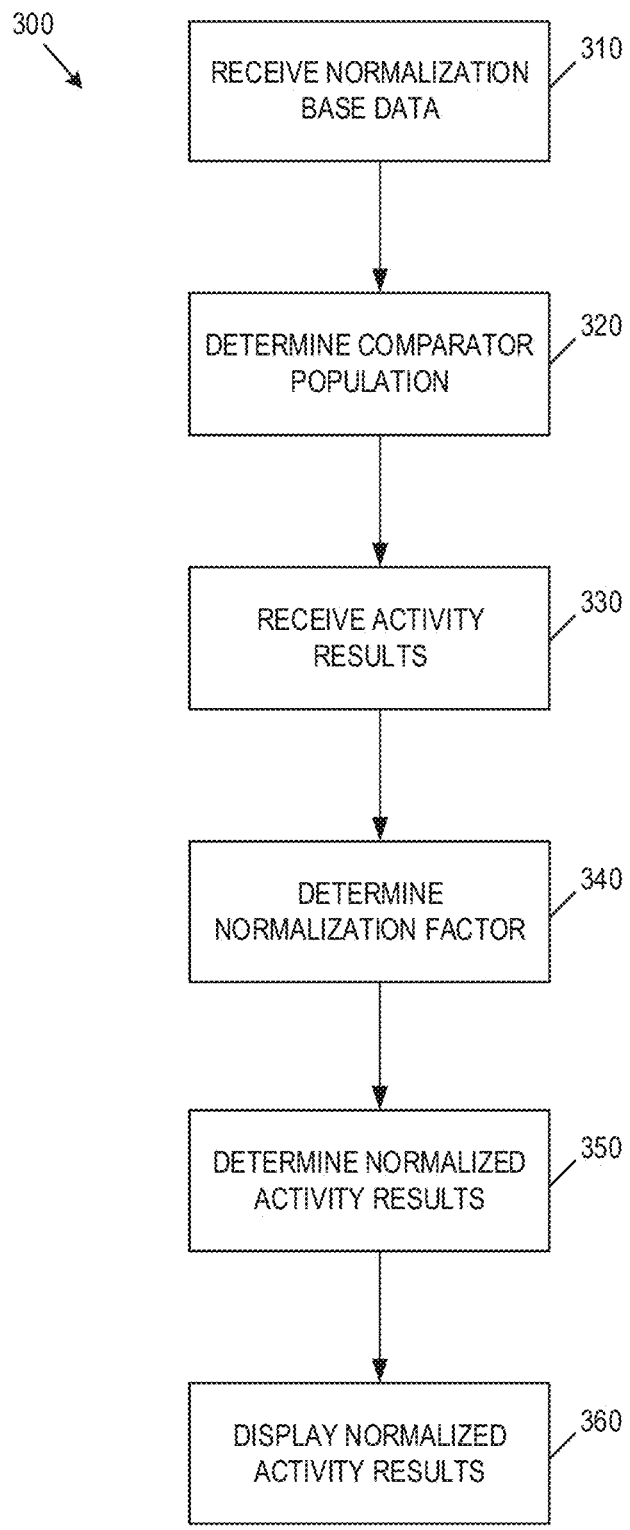
FIG. 3 shows a flowchart of an example embodiment of a process for generating normalized activity results that can be implemented by the systems of FIG. 1 and FIG. 2.

Referring now to FIG. 3, shown therein is a flowchart of an example process 300 for normalizing activity results. Process 300 is an example fitness normalization process that can be implemented by system 100 and/or system 200. In general, process 300 may be implemented by providing a mobile application from a server such as sever 106/206 for installation on the user devices 102/202.

Figure 9:
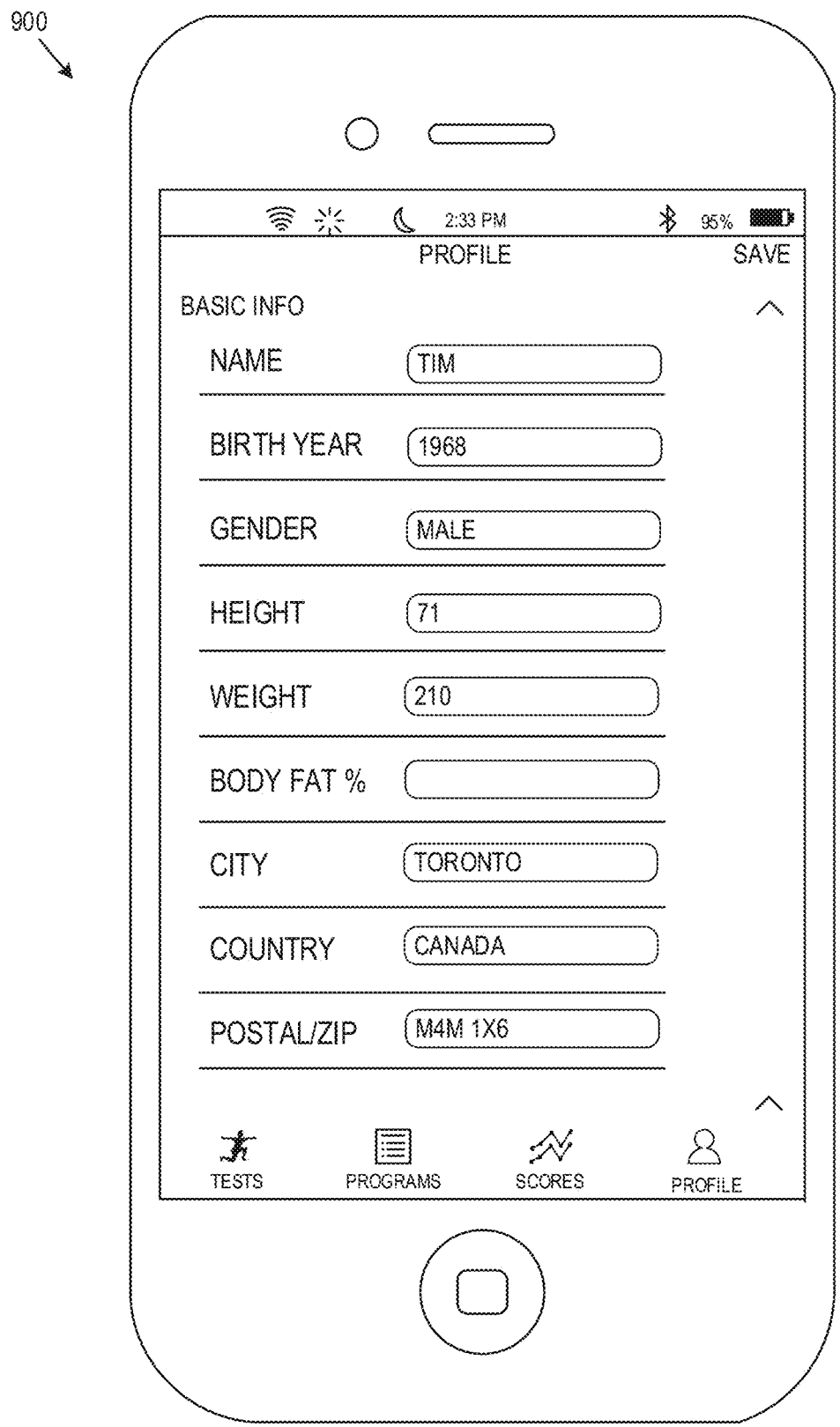
FIG. 9 shows an example of a user interface for collecting demographic user data from a user displayed on a user device.
Figure 10:
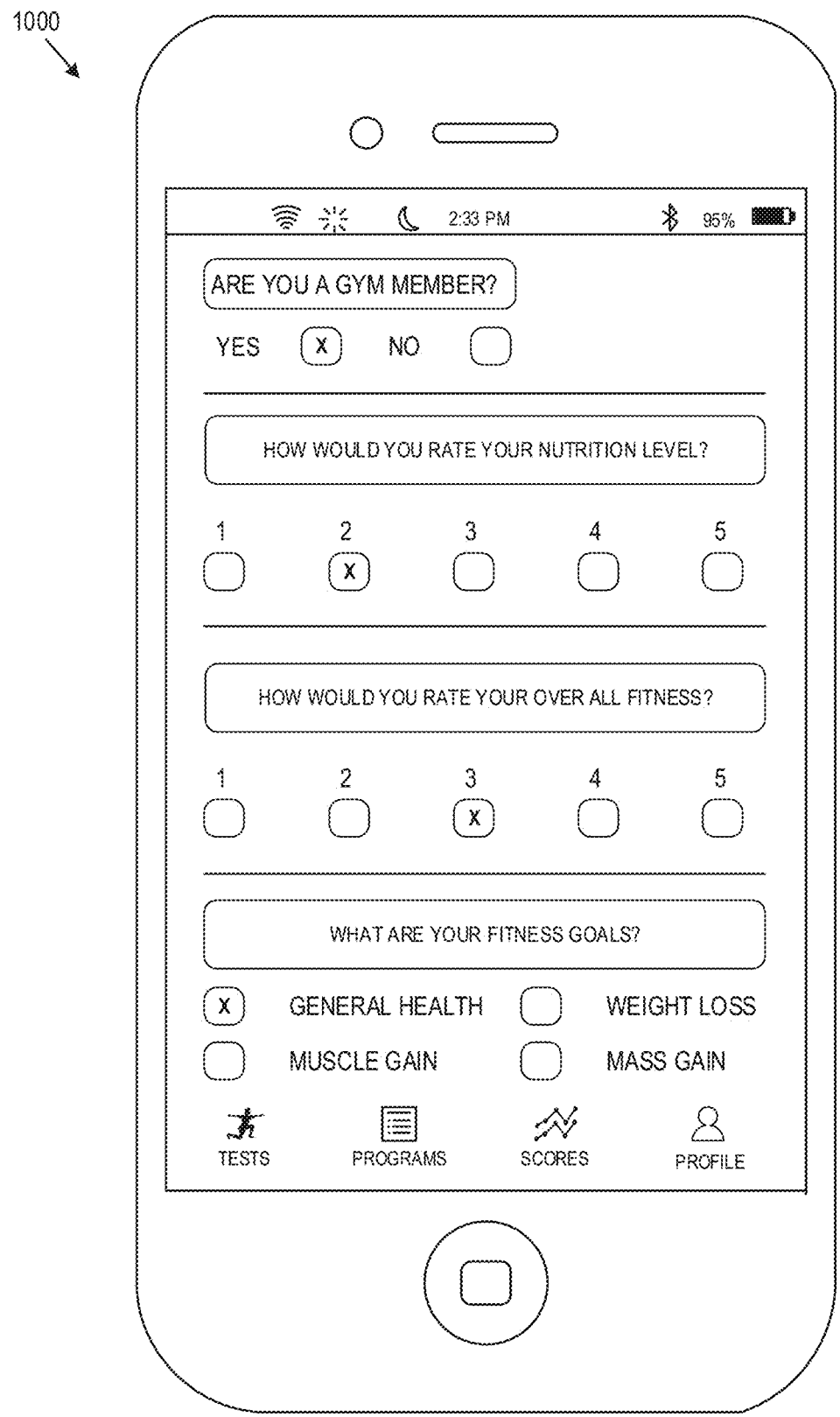
FIG. 10 shows an example of a user interface for collecting lifestyle user data from a user displayed on the user device.
Figure 11:
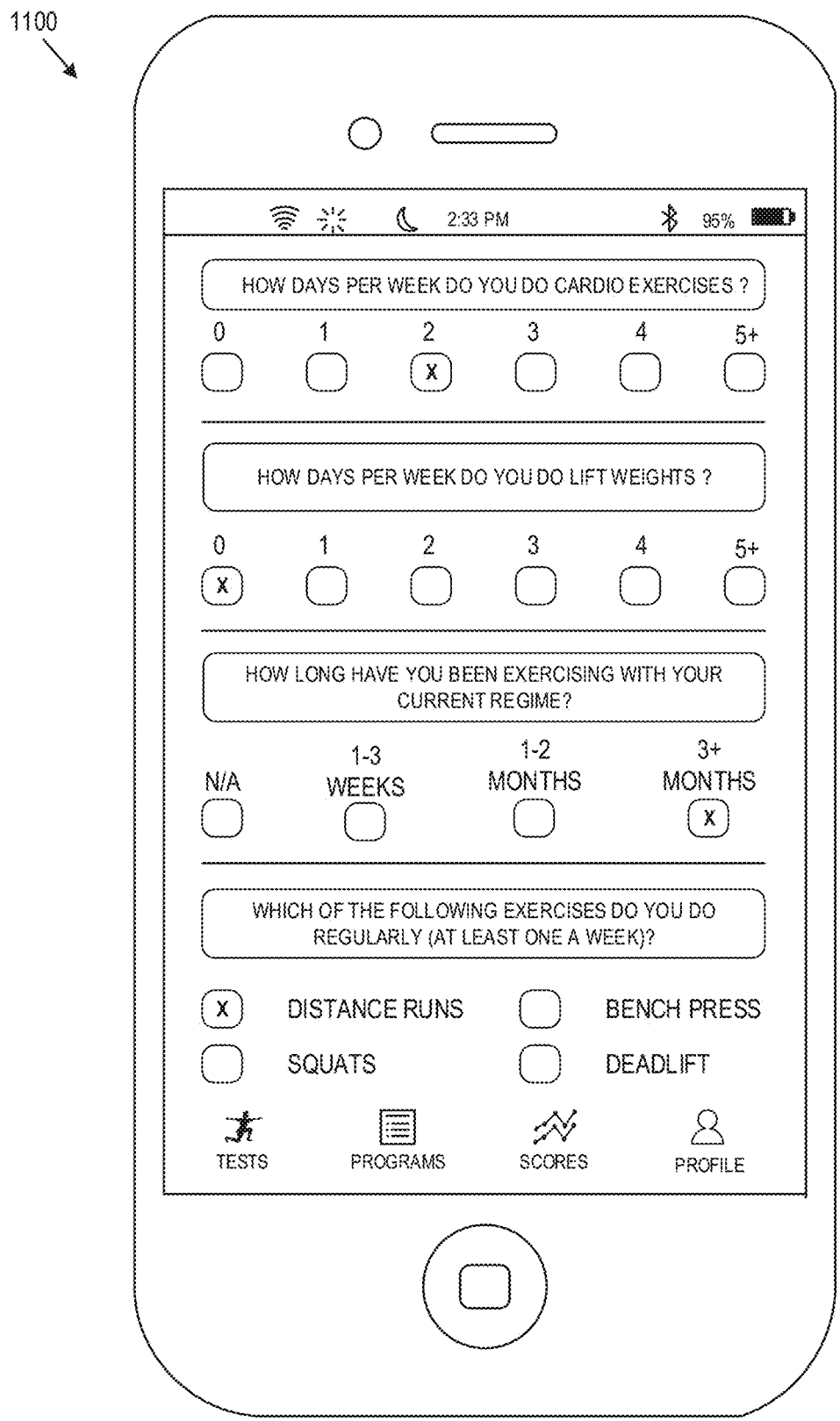
FIG. 11 shows an example of a user interface for collecting fitness regime user data from a user displayed on the user device.

At 310, normalization base data is received for a user using an application on the computing device associated with that user. The normalization base data may be received at user devices 102/202 and/or servers 106/206. For example, the user device 102 may install the fitness normalization application and display a series of user interfaces to collect the normalization base data from the user (examples of which are shown in FIGS. 9-11). Alternatively, in some cases the user may access a user interface provided by the server 106, for example on a web page over the internet.

The normalization base data for the user includes at least one normalization dimension. In some cases, the normalization base data may include user base data for a plurality of normalization dimensions. Examples of normalization dimensions include one or more demographic dimensions, one or more lifestyle dimensions, and one or more fitness regime dimensions. The normalization base data for a user may include demographic user data for demographic dimensions such as age, sex, height, weight, location, race, ethnicity and the like. The normalization base data for a user may include lifestyle user data for lifestyle dimensions such as exercise frequency, exercise intensity/exertion level, nutrition level, sleep patterns, and the like. The normalization base data for a user may include fitness regime user data for fitness regime dimensions such as fitness regime type, activity types, exercise regime duration and the like.

In some cases, the normalization base data for the user can be collected or updated automatically using user device 102 and/or the activity tracking device 150. For example, normalization base data such as the user's exercise frequency or sleep patterns could be monitored automatically using the activity tracking device 150 or user device 102, e.g. using a FitBit™ or Apple Watch for example. Such aspects of the user's normalization base data may be updated to more accurately reflect the user's current lifestyle. This may correct normalization base data that was input by a user on an aspirational rather than factual basis, or that has changed over time.

The normalization base data may be collected from a user through user interfaces generated by the mobile application, such as a series questions or pre-populated checklists. In some cases, each normalization base data input received from the user may be assigned a base value. The base values for the user may be used to define the normalization base data, e.g. by calculating normalization base scores in one or more normalization dimensions. For example, a series of base values may be collected from a user corresponding to the user's exercise frequency or activity types. These base values may be used to determine the normalization base data for a user's exercise frequency dimension or activity type dimension. In some cases, these base values may also be used to identify fitness regime user base data for the user.

The normalization base data may be stored on the storage device 118. The normalization base data can also be transmitted to the server 106, and stored in database 128. The normalization base data, along with activity results collected for the user can then be analyzed by analysis module 126 for various purposes. For example, as described with reference to FIG. 8 below, the normalization base data for a plurality of normalization users can be analyzed to define normalization populations and define normalization factors.

At 320, the user device 102 determines a comparator population for the user. The comparator population can typically be defined by the server 106, for example as described with reference to FIG. 8 below. The comparator population can be defined to include users having normalization base data within a comparator range.

Typically, the comparator population for the user is determined such that at least some of the normalization base data for the user is outside the comparator range. That is, the comparator population can be selected to allow the user to normalize their activity results to fairly compare themselves with users having different normalization base data.

In some cases, the comparator population may be determined automatically. For example, a default comparator population that represents a more active lifestyle, e.g. greater exercise frequency may be selected. Normalized activity results generated using the default comparator population may motivate the user to engage in a more active lifestyle.

Figure 19:
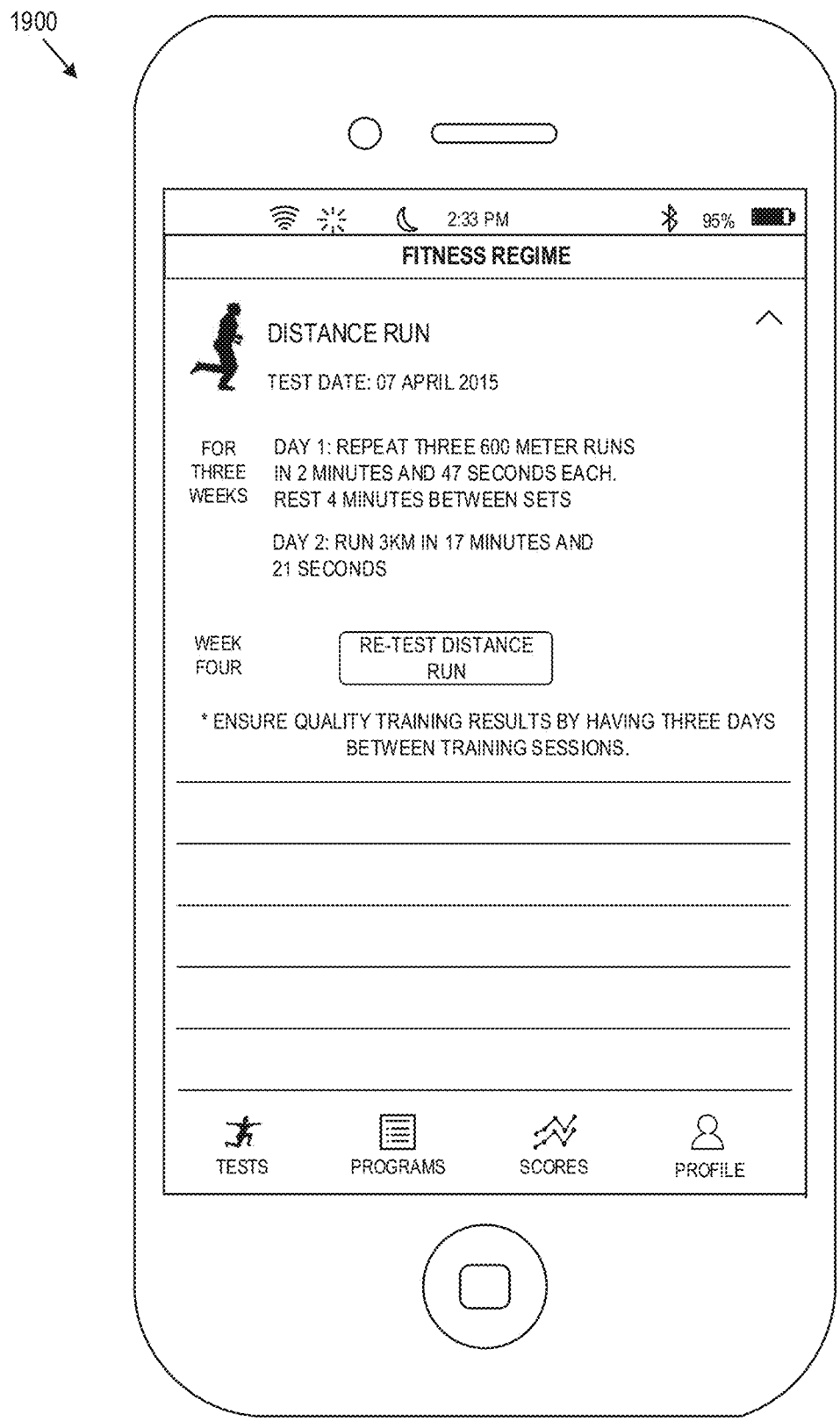
FIG. 19 shows an example of a user interface displaying a suggested fitness regime to the user on the user device.

In some cases, the comparator population may be determined for the user based on the user's fitness goals. For example, if the user identifies improving their upper body strength as a fitness goal, the comparator population may be selected as a fitness regime or exercise frequency suited to that goal. This may motivate the user to undertake that particular fitness regime to reach their fitness goals. In some cases, various activities and activity levels of the target fitness regime can be displayed to the user, as shown in FIG. 19. This may facilitate the user's transition to a new fitness regime.

In some cases, the user may select a comparator population. For example, the user may be interested in how their activity results would translate if they were 6 inches taller, 20 years younger, or more active. The user may select a comparator population with a comparator range that includes the normalization base data of interest. The resulting normalized activity results would let the user fairly compare themselves to users with different demographics or lifestyles.

At 330, the user device 102 receives at least one activity result for the user. The received activity results generally correspond to normalization activities that have been performed by the user. In some cases, the activity results can be input manually by a user into user device 102.

In other cases, one or more activity results can be automatically detected by user device 102 or an activity tracking device 150 in communication with user device 102. For example, the user may perform a normalization activity using exercise equipment such as a treadmill or a stationary bike. The exercise equipment may track the results attained by the user. The user device 102 may communicate with the exercise equipment to automatically detect the user's activity results.

In some cases, the activity tracking device 150 may track the user's cadence or motion, e.g. using an inertial motion sensor. In such cases, the user may indicate that they are performing a normalization activity (or one may be detected automatically). The activity tracking device 150 can then monitor the user's activity result and automatically transmit the activity results to the user device 102.

In some cases, the normalization activities for the user may be determined by the user device 102 or the server 106. For example, the normalization activities may be selected based on the user's normalization base data and/or the comparator population. An example sub-process for determining normalization activities for a user will be described in further detail with reference to FIG. 4 below.

In some cases, the user device 102 or the server 106 may monitor activity results for the user over time. The normalization base data may then be adjusted based on the monitored results. For example, the user device 102 or the server 106 may store activity results received for the user over a period of time. The stored activity results may be analyzed to determine if various aspects of the user's normalization base data has changed such as the user's activity level, exertion level, activity types etc.

At 340, at least one normalization factor is determined for the user. The normalization factor can be determined based on the normalization base data received for the user at 310 and the comparator population determined at 320.

In some cases, the user may be assigned to a user population based on the normalization base data received at 310. The user population may be defined to include users having normalization base data in a user population range for one or more normalization dimensions. In general, the comparator population determined at 320 is determined so that, for at least one of the normalization dimensions, the user population range and the comparator population range are different.

The user population may have a plurality of activity results associated therewith. For example, a plurality of normalization users having normalization base data falling within the user population range may be identified. Activity results from the plurality of normalization users can be collected using the mobile application. These activity results can then be transmitted to the server and associated with the user population.

In a similar manner, the comparator population can also have activity results associated therewith. Typically, when normalizing activity results for a user the user population range may be different from the comparator range of the comparator population. That is, the comparator population will typically be chosen to include users having at least some difference in normalization base data compared to the user (i.e. a difference in at least one normalization dimension).

The normalization factors can be determined based on the activity results associated with the user population and activity results associated with the comparator population. For example, average activity results associated with the user population and average activity results associated with the comparator population can be identified. The normalization factors can then be determined by comparing the average activity results for the user population and the average activity results for the comparator population. In some cases, at least one normalization factor may be adjusted based on the user's normalization base data. For example, where the user population includes a range of ages or a range of exercise frequency, the normalization factor may be adjusted to account for the user's specific age or exercise frequency.

In some cases, the normalization base data may include user base data for a plurality of normalization dimensions. In such cases, the user device 102 may be configured by the fitness normalization application to determine a normalization factor for each normalization dimension. For example, the normalization dimensions may include a weight dimension, an age dimension, an activity level dimension, and a fitness regime dimension, and a normalization factor may be determined for each dimension based on the user base data for that dimension and the activity results associated with the comparator population over that dimension. Further details of a sub-process for defining normalization factors will be described below with reference to FIG. 8.

At 350, the user device 102 determines normalized activity results for the user by adjusting the at least one activity result using the normalization factors determined at 340. Examples of normalized activity results will be discussed in further detail below with reference to FIGS. 5-7. In effect, the normalized activity results indicate activity results expected for the user if the user's normalization base data changed to be within the comparator range. In some cases, the normalization factor may not be determined by the user device 102 directly, but the activity results can be normalized through communication with the server 106/206.

In some cases, the same normalization factors may be applied to each activity result to obtain the normalized activity results. In other cases, the normalization factors may include at least one activity-specific normalization factor for each of the normalization activity. In such cases, the activity results for each normalization activity can be adjusted using the activity-specific normalization factors for that normalization activity.

Figure 18:
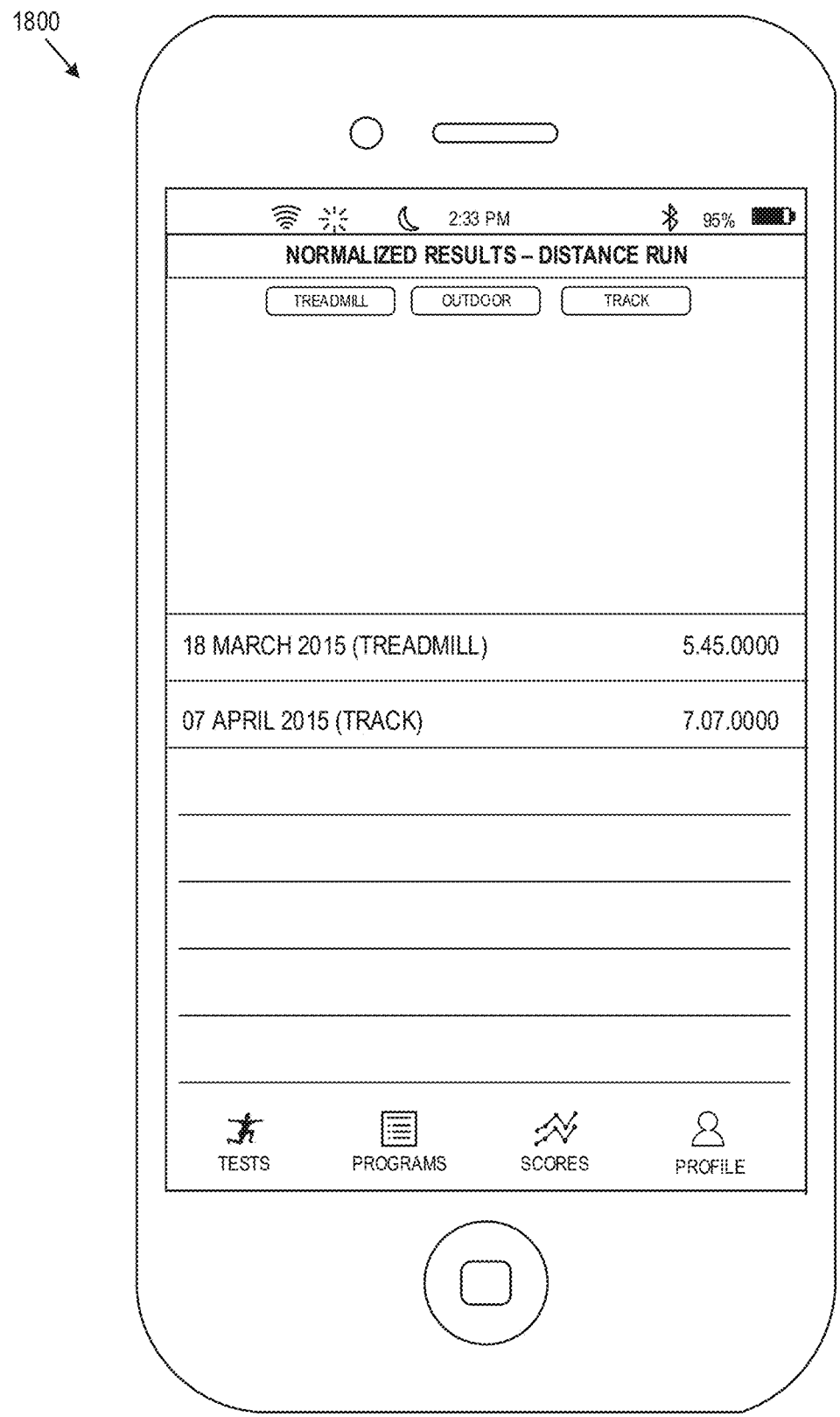
FIG. 18 shows an example of a user interface displaying normalized activity results corresponding to the activity results of FIG. 17 to the user on the user device.

At 360, the user device 102 can display the normalized activity results to the user on display 116. An example user interface showing normalized activity results is shown in FIG. 18, discussed further below. The normalized activity results may indicate to the user how their exercise and fitness efforts may translate if they adjust their lifestyle or fitness regime to match that of the comparator population. In some cases, the normalized activity results may indicate to the user how their activity results might differ if their demographic base data was different, e.g. if they were younger or taller. In some cases, the normalized activity results may provide a combination thereof.

Displaying normalized activity results to the user may provide motivation to adjust aspects of the user's lifestyle or fitness regime. This may in turn motivate the user to become healthier or more active. As well, the normalized activity results may allow users to motivate one another through friendly competition where activity results are compared fairly for different demographics, lifestyles, and/or fitness regimes.

Figure 4:
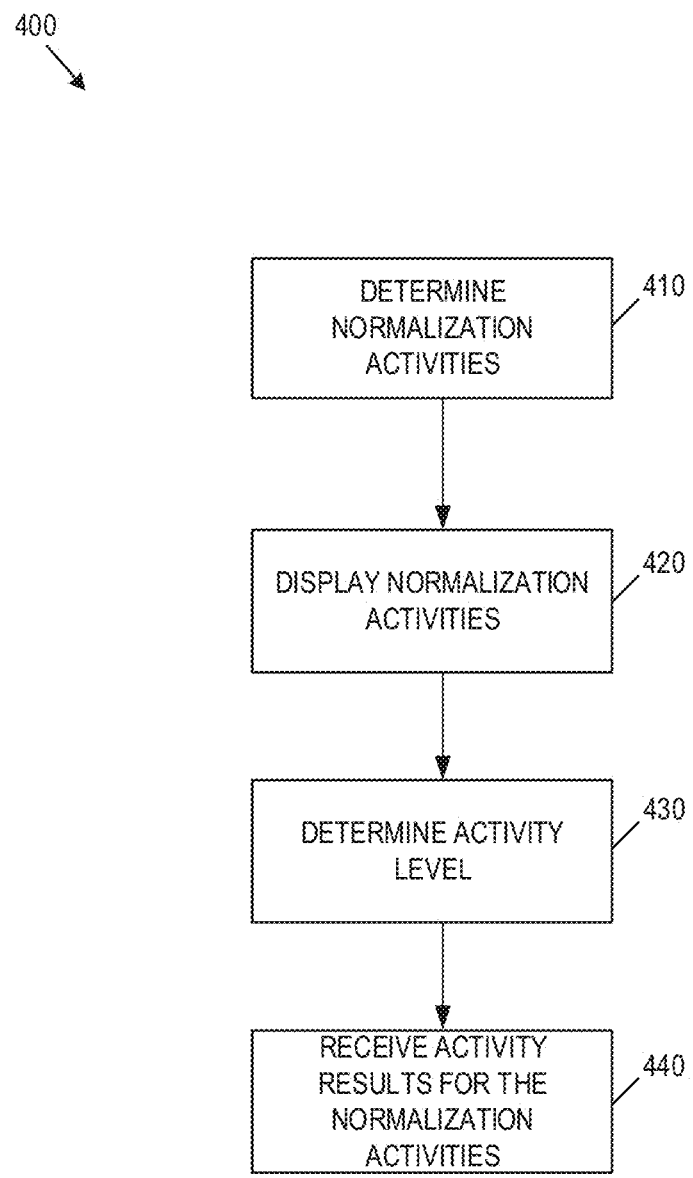
FIG. 4 shows a flowchart of an example embodiment of a sub-process for generating normalized activity results that can be used with the process for generating normalized activity results of FIG. 3.

Referring now to FIG. 4, shown therein is a flowchart of an example sub-process 400 for normalizing activity results that can be used with process 300.

At 410, the user device 102 can determine at least one normalization activity for the user. In some embodiments, the user may select one or more of the normalization activities to see how their results change for those activities when normalized. For example, the user may select normalization activities they often perform, such as a runner selecting a distance run normalization activity or a weight-lifter selecting a deadlift normalization activity.

In some embodiments, the normalization activities can be determined based on the comparator population. The normalization activities may be selected based on activity types or fitness regime data in the comparator range. These normalization activities may reflect activities typically performed by users having normalization base data in the comparator range. For example, when the comparator population includes a cycling fitness regime a leg press normalization activity could be determined, whereas for a weight-lifting fitness regime a deadlift normalization activity could be determined.

In some embodiments, the at least one normalization activity may be determined based on the normalization base data for the user. The normalization activities may be determined based on activity type user base data or fitness regime data as above. In some cases, the at least one normalization activity may be determined for the user based on normalization base data or previous activity results. In some cases, the normalization activities may be selected based on fitness goal data associated with the user.

At 420, the user device 102 can display the normalization activities determined at 410 to the user on display device 116. Examples of user interfaces displaying normalization activities are discussed below with reference to FIGS. 13-15. The user can then select one of the display normalization activities to indicate that the activity is being performed, to input activity results, or to receive instruction on the normalization activity to be performed.

At 430, the user device determines an activity level for at least one of the normalization activities determined at 410. An indication of the determined activity level can be shown to the user on display device 116. The indication informs the user that they should perform the normalization activity at the activity level displayed.

In some embodiments, the activity level may indicate that the normalization activity should be performed with a specified weight level. For example, if the normalization activity is a deadlift, the activity level may identify the amount of weight the user should deadlift. If the normalization activity is a distance run, the activity level may identify the length of the run to be performed, or the pace to be maintained by the user.

In some cases, the activity level for a user may be determined based on the normalization base data received from the user. In such cases, the activity level may also be referred to as a user-specific activity level. The activity level may be determined based on user body weight data included in the normalization base data received for the user. For example, where the activity level is a specified weight, the specified weight may be determined based on the user's body weight. This may ensure that user's having different normalization base data are performing activities at a level that allows their results to be accurately normalized to users having other normalization base data.

For example, a sedentary user weighing 115 lbs may be unable to deadlift 200 lbs. As a consequence, the user's activity results at that activity level may not provide any meaningful data that can be normalized with a comparator population. Accordingly, a more suitable deadlift amount may be determined for the user to enable the user to achieve meaningful activity results which can then be normalized.

In some cases, the normalization activity determined for a user can be used to assess the user's fitness in one or more fitness categories. Examples of fitness categories may include endurance, stamina, speed, acceleration, strength, power and the like.

For example, when the normalization activities are displayed at 420, a plurality of fitness categories may be associated with each normalization activity. The user may select one or more fitness categories for each normalization activity, e.g. using input device 114 on user device 102. The activity level for each normalization activity may then be determined based on the selected fitness category and displayed to the user.

In some cases, the activity level determined for the user may be determined based on the user's normalization base data and the fitness category being assessed. For example, for activity types involving weights, one or more lower weight levels may be specified to assess the user's stamina or endurance, while one or more higher weight levels may be specified to assess the user's strength or power. An example user interface displaying multiple activity levels for a single normalization activity is discussed below with reference to FIG. 16.

The definition of a particular activity level may vary depending on the particular normalization activity, even where the same fitness category is being assessed. As well, a particular activity level may include a range of specific levels (such as a range of +/− 5% of a weight level identified), to allow users to select activity levels that can be performed using weights normally found in a gym environment. In some embodiments, the bench press normalization activity may use an activity level of about 60% of the user's body weight to assess stamina, an activity level of about 80% of the user's body weight to assess endurance, an activity level of about 100% of the user's body weight to assess strength, and an activity level of about 120% of the user's body weight to assess power. In some embodiments, the back squat normalization activity, however, may use an activity level of about 75% of the user's body weight to assess stamina, an activity level of about 100% of the user's body weight to assess endurance, an activity level of about 125% of the user's body weight to assess strength, and an activity level of about 150% of the user's body weight to assess power.

In some embodiments, a deadlift normalization activity may also use an activity level of about 75% of the user's body weight to assess stamina, an activity level of about 100% of the user's body weight to assess endurance, an activity level of about 125% of the user's body weight to assess strength, and an activity level of about 150% of the user's body weight to assess power. In some embodiments, a seated military press normalization activity, however, may use an activity level of about 40% of the user's body weight to assess stamina, an activity level of about 50% of the user's body weight to assess endurance, an activity level of about 60% of the user's body weight to assess strength, and an activity level of about 70% of the user's body weight to assess power.

For one example, a user's endurance fitness category may be assessed. For a user with normalization base data indicating they are 25 years old with a vigorous activity level and a runner fitness regime, a long distance run normalization activity may be selected for the user with an activity level of 10 kilometers. For a user with normalization base data indicating that they are 70 years old with low activity level and an unspecified fitness regime, an activity level with a shorter duration or length may be selected. Alternatively, a specified speed may be selected for the distance run normalization activity while a specific cadence may be selected for a spinning normalization activity when assessing different fitness categories for a user. These activity levels may also be user-specific activity levels determined based on the normalization base data for the user.

In some embodiments, the activity level may be defined to include one or more of a duration level and an exertion level. The exertion level may also include an activity modification in some cases. For example, a push up normalization activity may assess a user's stamina using a duration level of 5 minutes and no specified exertion level. The push up normalization activity may use a continuous exertion level and an unlimited duration to assess the endurance fitness category, and a 1 minute duration and high intensity exertion level to assess the strength category. To assess the power fitness category, the push up normalization activity may include an unlimited duration with a modification to the push up normalization activity such as instructing a user to initially perform a standard push up, and when the user's arms approach full extension the user should accelerate can cause their hands to be released from the floor, cross their arms (have their right hand touch their left shoulder and left hand touch their right), and then quickly uncross their arms and repeat the movement continuously for an unlimited duration.

For another example, the mobile application may display a pull up normalization activity to a user. To assess the stamina fitness category, the mobile application may determine an activity level with a 5 minute duration. The pull up normalization activity may use a continuous exertion level and an unlimited duration to assess the endurance fitness category, and a 1 minute duration and high intensity exertion level to assess the strength category. The pull up normalization activity may indicate to a user to add 10% of their body weight and repeat the activity for an unlimited duration to assess the power fitness category.

For a further example, the mobile application may display a sit up normalization activity to a user. To assess the stamina fitness category, the mobile application may determine an activity level with a 5 minute duration. The sit up normalization activity may use a continuous exertion level and an unlimited duration to assess the endurance fitness category, and a 1 minute duration and high intensity exertion level to assess the strength category. The sit up normalization activity may indicate to a user to add 10% of their body weight and repeat the activity for an unlimited duration to assess the power fitness category.

At 440, activity results are received from the user at user device 102 using the fitness normalization application. The activity results received at 440 correspond to the user having performed the normalization activity determined at 410 at the activity level determined at 430. In general, the activity results can be received in the same manner as 340 above. These activity results can then be normalized in the same manner as described above with reference to FIG. 3.

Referring now to FIG. 5, shown therein is a diagram illustrating an example table 500 of fitness results and normalized fitness results for users having different demographic base data and lifestyle base data. Table 500 is an example of normalized fitness results generated with a comparator population having a comparator range of age 30-35 yrs and activity level vigorous. Each user has performed a bench press normalization activity at a first activity level.

The activity results 530 may be used to assess each user's fitness for the particular activity in a fitness category. The activity results 530 shown may correspond to a bench press normalization activity for assessing the user's endurance. Accordingly, the first activity level for each user was determined based on the normalization base data for that user. If a different fitness category were being assessed, a different activity level may be determined for the normalization activity.

In FIG. 5, the activity level has been determined as a weight for the bench press, where the weight is based on user body weight data included in the normalization base data for that user. Here, the first activity level indicates to the user that a weight of 60% of that user's body weight should be bench pressed. Each user may have received an indication in the fitness normalization application of the activity level indicating that the weight to be bench pressed should be 60% of the user's body weight. The user may indicate when providing the activity results 530 that the activity was performed at the first activity level.

If, say, the fitness category being assessed was the user's power, the activity level may indicate a higher weight to bench press. For example, the user device 102 may display an indication of the activity level that shows the user to perform the bench press at 120% of the user's body weight.

Each user whose results are shown in Table 500 has been assigned to at least one user population. Two users have been assigned to a user population with a sedentary lifestyle category, two users to a user population with a light active lifestyle category, two users to a user population with a moderately active lifestyle category, and two users to a user population with a vigorously active lifestyle category. The lifestyle category user populations shown here are examples only, and it should be apparent that the lifestyle categories can be defined in many different ways, based on the normalization base data received from a plurality of normalization users.

The users shown in each lifestyle category 510 may also have been assigned to a user population based on the age 520 included in the normalization base data. The users associated with each lifestyle category 510 in table 500 include a younger user of age 30, and an older user of age 60.

Activity results 530 have been collected for each user. The activity results 530 were collected for each user for the bench press normalization activity. As may be expected, the users associated with the sedentary lifestyle category and older age groups had lower results, while the users associated with the vigorous lifestyle category and younger age had higher results. However, using embodiments of the normalization systems and methods described herein, the results for the users can be normalized to generate normalized activity results that can be fairly compared across user populations.

The age-normalized results 540 were normalized for a comparator population with an age range of 30-35 years. Accordingly, the age-normalized results 540 were the same as the activity results 530 for the users' aged 30, because the comparator population has a comparator range that includes those users. Accordingly, a minimal normalization factor, or no normalization factor may be determined for such users. However, the older users age 60 see their age-normalized results 540 adjusted based on the normalization factors determined for those users. In the example shown, the age-normalized results 540 of the older users are increased relative to the activity results 530. For example, although the younger vigorously active user achieved higher results 530, after normalizing for age, the older vigorously active user achieved higher age-normalized results 540.

The normalized results 550 were normalized using a comparator population with an age range of 30-35 years and a vigorously active lifestyle. The vigorously active users' normalized results 550 were not changed with respect to the age-normalized results 540, as the additional normalization dimension of the comparator range includes the normalization base data associated with those users. However, for the users with lower activity levels, the normalized results 550 were higher than the results 530. For example, although the sedentary 60 year old was only able to complete two bench presses, the normalized activity results 550 indicate that if that user were to adjust their lifestyle (and were a few years younger) they may be able to complete 20 bench presses. These normalized activity results 550 might be used by an older user to allow them to safely compete against younger friends and relatives.

Referring now to FIG. 6, shown therein is a therein is a diagram illustrating another example table 600 of activity results and normalized activity results for users in various user populations. Here, the activity results 630 and normalized activity results 640 are displayed for three different users 610A-C.

Each user 610 has performed the deadlift normalization activity at each of four activity levels 620. Each activity level 620 indicates a user-specific weight level each user 610 should deadlift. In table 600, the activity levels are defined based on user body weight data for each user. For example, at activity level 2 the user 610A has provided activity results 630 corresponding to a deadlift normalization activity performed at 155 lbs, while the user 610B has provided activity results 630 corresponding to a deadlift normalization activity performed at 175 lbs. In other embodiments, the activity levels may be determined as a consistent activity level for each user, e.g. a specific weight.

In some cases, each activity level 620 may be used to assess a user 610 in a different fitness category. For example, activity level 1 may be used to assess stamina, activity level 2 may be used to assess endurance, activity level 3 may be used to assess strength, and activity level 4 may be used to assess endurance.

As table 600 indicates, the normalization factors for the users may be different. For example, although the user 610A achieved a lower activity result 630 at the first activity level than the user 610C, the normalized activity results for user 610A and user 610C are the same at the first activity level.

Referring now to FIG. 7, shown therein is a diagram illustrating an example table 700 of activity results 740 and normalized activity results 750 for a user with two different comparator populations 710A and 710B. In table 700, the user has been assigned to a user population 760 with normalization base data indicating a runner fitness regime.

The first comparator population 710A was determined to have a comparator range including a cycling fitness regime, while the second comparator population 710B was determined to have a comparator range including a weightlifting fitness regime. For example, these comparator populations 710 may have been chosen by the user because they are interested in comparing activity results with friends having different fitness regimes, or because they are considering adjusting their own fitness regime.

A plurality of normalization activities 720 were determined for the user. As mentioned above, in some cases the normalization activities 720 can be determined based on the user population 760 and/or the comparator populations 710A/710B. For example, the distance run normalization activity may be determined based on the runner user population 760 as a normalization activity typically performed by users in that population.

In table 700, the normalization activities determined for both the cycling comparator population 710A and the weightlifting comparator population 710B include the squat, bench press, and distance run normalization activities. However, a leg press normalization activity was determined for the cycling comparator population 710A, while a deadlift normalization activity was determined for the weightlifting comparator population 710B. These normalization activities may correspond to activity typically performed by users having normalization base data in the comparator range.

In table 700, an activity level 730 was determined for each normalization activity 720. For example, the user may be interested in seeing how their stamina might be affected if they pursue a cycling fitness regime, and in seeing how their power might change if they pursue a weightlifting regime. As a consequence, the normalization activities were performed at activity level 1 for the cyclist comparator population and at activity level 4 for the weightlifter population (it should be apparent, however, that once the results at any activity level are received they can be normalized to the desired comparator population).

The user can receive an indication of the activity results 740 and normalized activity results 750 on the user device 102. The user may then use these normalized activity results 750 to select a particular fitness regime, or to compare results with friends.

Figure 8:
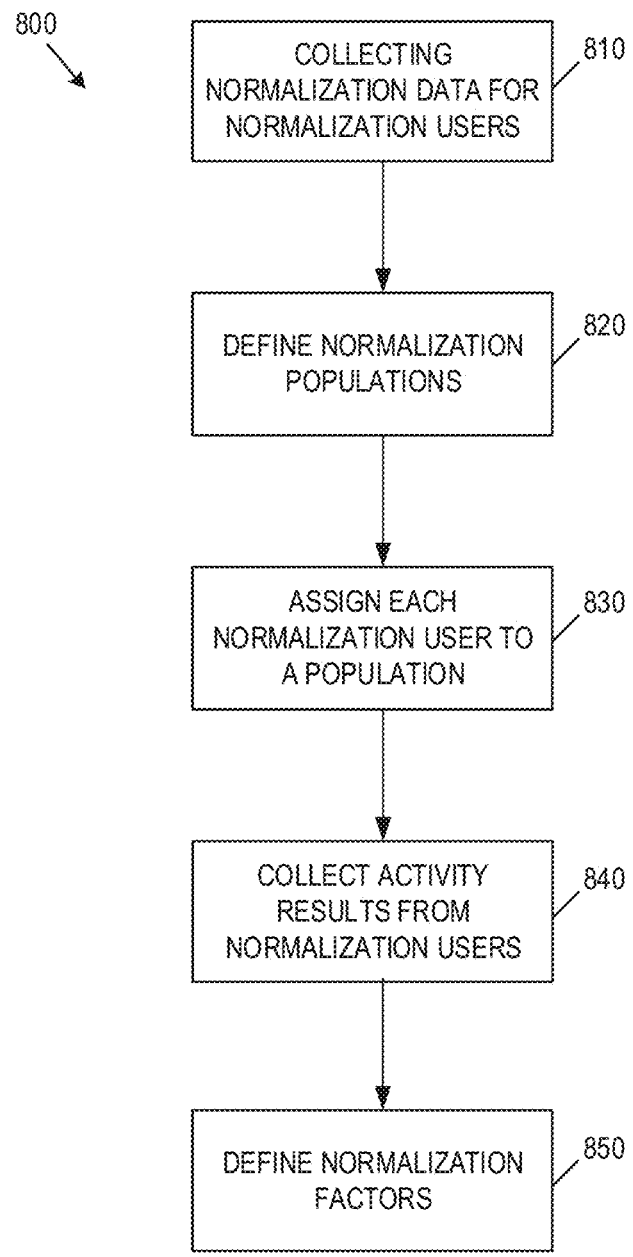
FIG. 8 shows a flowchart of an example embodiment of a process for defining normalization factors that can be used with the process for generating normalized activity results of FIG. 3.

Referring now to FIG. 8, shown therein is a flowchart of an example process 800 for defining normalization factors that can be used with process 300. The normalization factors can be determined based on activity results collected from a plurality of users. For example, the activity results can be collected from a plurality of normalization users over an extended period of time. The activity results can be collected for normalization users having a wide range of normalization base data. These activity results can be analyzed, and normalization factors between different groups of normalization users can be determined.

At 810, normalization base data for a plurality of normalization user can be collected. The normalization base data can be collected from the user device 202 associated with each normalization user. The normalization base data for each normalization user may include user base data for a plurality of normalization dimensions, as described above.

At 820, the server 106 can define a plurality of normalization populations, where each normalization population has a corresponding population base data range. In some cases, each normalization population may have a population base data range that corresponds to a single normalization dimension. For example, a first normalization population may include all users age 30-35, while a second normalization population may include all users having a particular fitness regime, e.g. weightlifting.

In some cases, the normalization populations may include a population base data range for a plurality of normalization dimensions. For example, a normalization population may have a population base data range that includes all users aged 20-25, who have sedentary exercise frequency, and poor nutrition levels.

In some cases, the normalization populations may be identified based on clusters of normalization users. For example, the server 106 may identify a cluster of users having normalization base data within a small range over a plurality of normalization dimension. Such clusters of users may be used to identify normalization populations having a population base data range over the plurality of normalization dimensions.

At 830, each normalization user can be assigned to at least one of the normalization populations. Each normalization population to which a normalization user is assigned will have a population base data range corresponding to the normalization base data collected for that user.

In some cases, each user population may include a first plurality of normalization population. Each normalization population in the first plurality of normalization populations may correspond to a particular normalization dimension. The comparator populations and user population discussed above may be similarly defined. For a particular normalization user who wants to normalize activity results with a particular comparator population, the comparator population may include a second plurality of normalization populations, with one normalization population for each normalization dimension. The second plurality of normalization populations will typically be different from the first plurality of normalization populations for that user, so that the comparator population includes users having at least slightly different normalization base data from the user whose activity results are to be normalized.

At 840, the server 106 can collect at least one activity result from normalization users in each of the normalization populations. The server 106 can collect activity results from each of the normalization users mentioned at 810. The server 106 may associate the activity results collected for each normalization user with the at least one normalization population to which that normalization user was assigned. As will be apparent, in some embodiments the activity results collected for a normalization user can be associated with a plurality of normalization populations, one for each normalization dimension in normalization base data collected for the user.

In some cases, the activity results for each of the normalization users can be monitored over time. The monitored activity results may be analyzed and the normalization base data for a particular normalization user may be updated based on the monitoring activity results. In some embodiments, the particular normalization user may be removed from one of the normalization populations to which that user was assigned and re-assigned to a different normalization population based on the updated normalization base data. This may occur, for example, where the user's exercise frequency or fitness regime has changed. This may also occur, for example, when the user ages. The activity results collected from that normalization user while that normalization user was assigned to a particular normalization population can remain associated with the same normalization population, as they were collected when that normalization user had normalization base data for that normalization population. Subsequent activity results may then be associated with the new normalization population to which that user is assigned.

At 850, the server 106 can define a plurality of normalization factors by comparing the activity results collected for the plurality of normalization populations. These normalization factors can be used to determine normalized activity results for a user, as explained above. In some cases, over time the server 106 may refine or re-define at least one of the normalization factors based on monitored activity results from the plurality of normalization users.

In some embodiments, the particular normalization factors determined for a user may have been defined by comparing the activity results for a first plurality of normalization populations corresponding to the user population with the activity results for a second plurality of normalization populations corresponding to the comparator population.

For example, the server 106 may identify a plurality of normalization population pairs. Each normalization population pair can include two different normalization populations from the plurality of normalization populations. For example, the two different normalization populations may reflect different base data ranges within a single normalization dimension. The server 106 may define normalization factors for each normalization population pair using the activity results collected for the normalization users assigned to each normalization population in that normalization population pair.

In some cases, the server 106 may repeat this process for each normalization population pair. The server 106 can store the plurality of normalization factors in the database 128. The server 106 may provide the normalization factors to the user device 102 for the relevant normalization population pair based on the user's normalization base data and the comparator population. In some cases, the server 106 may determine the normalization population pairs, and corresponding normalization factors, as required based on a request for normalized activity results from one of the user devices 102.

Referring now to FIG. 9, shown therein is an example of a user interface 900 displayed on a user device such as user device 102. User interface 900 is an example of a user interface that can be used to collect demographic user data from a user The user interface 900 includes a series of fields that can receive input from the user to collect the normalization base data. For example, the user interface 900 collects demographic user data for the demographic dimensions of age, height, weight, gender or sex, and location. In user interface 900, the location dimension is in fact three sub-dimension each providing a different level of specificity, such as country, city, and postal code or zip code. User interface 900 is merely an example, and in other embodiments various different methods of collecting normalization base data can be used. As well, in other embodiments, more or less demographic user data may be collected for a user.

Referring now to FIG. 10, shown therein is an example of a user interface 1000 displayed on a user device such as user device 102. User interface 1000 is an example of a user interface that can be used to collect lifestyle user data from a user.

User interface 1000 may include a series of fields or questions regarding the user's lifestyle. In some cases, the questions may include multiple pre-populated responses and the user may select the response most reflective of their lifestyle. For example, the user interface 1000 may include questions related to various lifestyle dimensions such as the nutrition level and activity level questions shown. In some embodiments, input received from the user at user device 102 may be used to determine the normalization base data for the user. For example, the user's input on user interface 1000 may suggest that the user has a moderate activity level, and a below average nutrition level. However, the input received from user may not be accurate, so in some cases, the user device 102 or server 106 may monitor the user's actions and activity results, e.g. using activity tracking device 150, to supplement or modify the normalization base data to more accurately reflect the user's lifestyle.

Other questions related to various lifestyle dimensions such as exercise frequency, exercise intensity/exertion level, sleep patterns, and the like may also be used. As well, it will be apparent that user interface 1000 is merely an example, and various other methods can be used to acquire normalization base data from the user. The user interface 1000 may also be used to collect other information from the user, such as whether the user is a gym member, and the user's fitness goals. This data may also be used in various embodiments of systems 100 and 200. For example, the user's fitness goals may be used to identify potential relevant comparator populations for the user, or to identify potentially relevant fitness regimes that may interest the user.

Referring now to FIG. 11, shown therein is an example of a user interface 1100 displayed on a user device such as user device 102. User interface 1100 is an example of a user interface that can be used to collect fitness regime user data from a user. For example, the user input shown on user interface 110 may suggest that the user has a runner or distance runner fitness regime.

User interface 1100 may include a series of fields or questions regarding the user's fitness regime. In some cases, the questions may include multiple pre-populated responses and the user may select the response most reflective of their current fitness regime. For example, the user interface 1100 may include questions related to various fitness regime dimensions such as a fitness regime type, activity types, activity levels, exercise regime duration, and the like. In some cases, more and different questions may be used, and the questions displayed on user interface 110 are merely exemplary.

Figure 12:
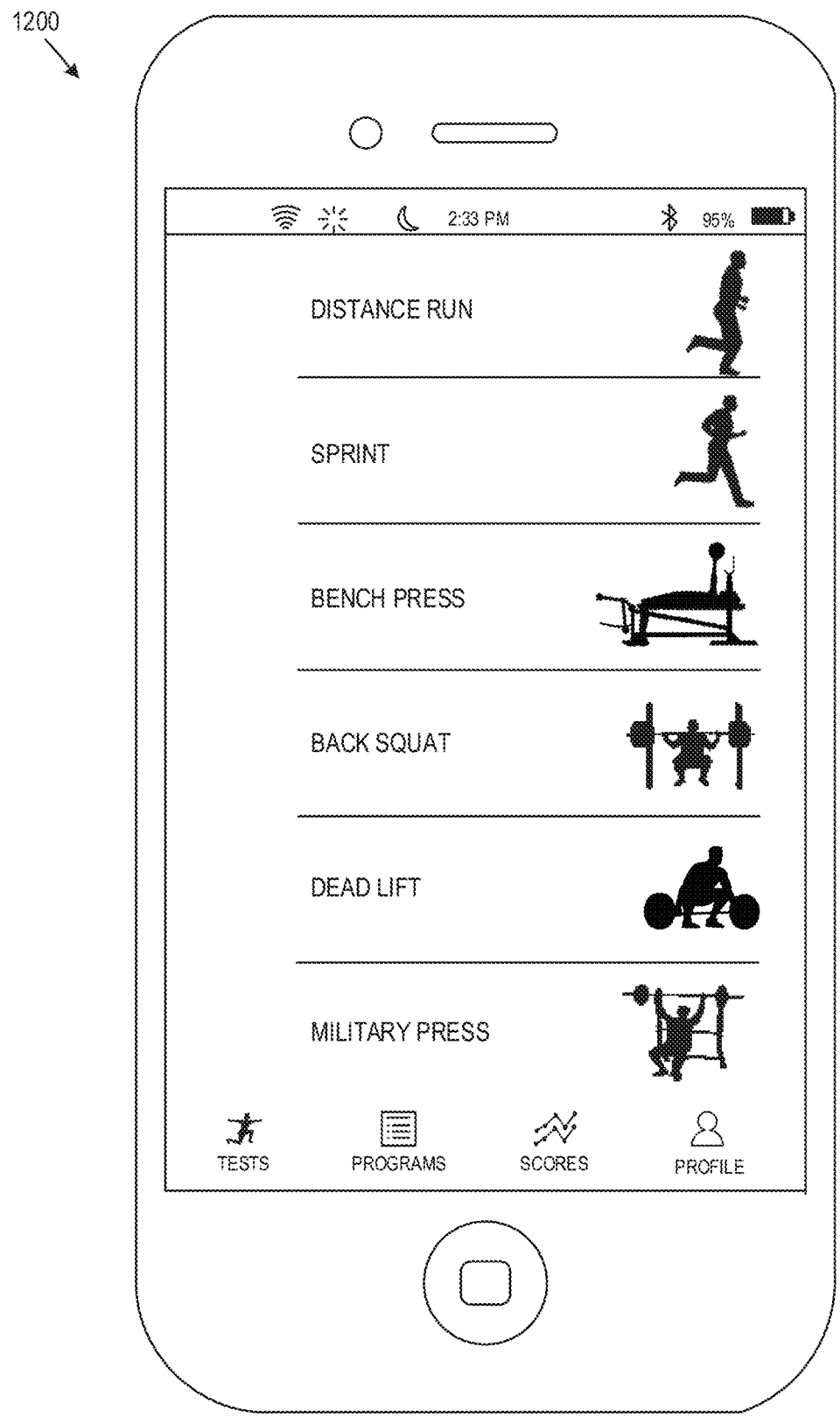
FIG. 12 shows an example of a user interface displaying examples of normalization activities to the user displayed on the user device.

Referring now to FIG. 12, shown therein is an example of a user device 1200 displayed on a user device such as user device 102. User interface 1200 is an example of a user interface displaying activities to the user. In some cases, the user may select the activities displayed on user interface 1200 to receive instruction on the performance of an activity. In other cases, the user may select one of the activities displayed to input an activity result for the selected activity. In some examples, user interface 1200 may be a list indicating normalization activities that have been determined for the user.

Figure 13:
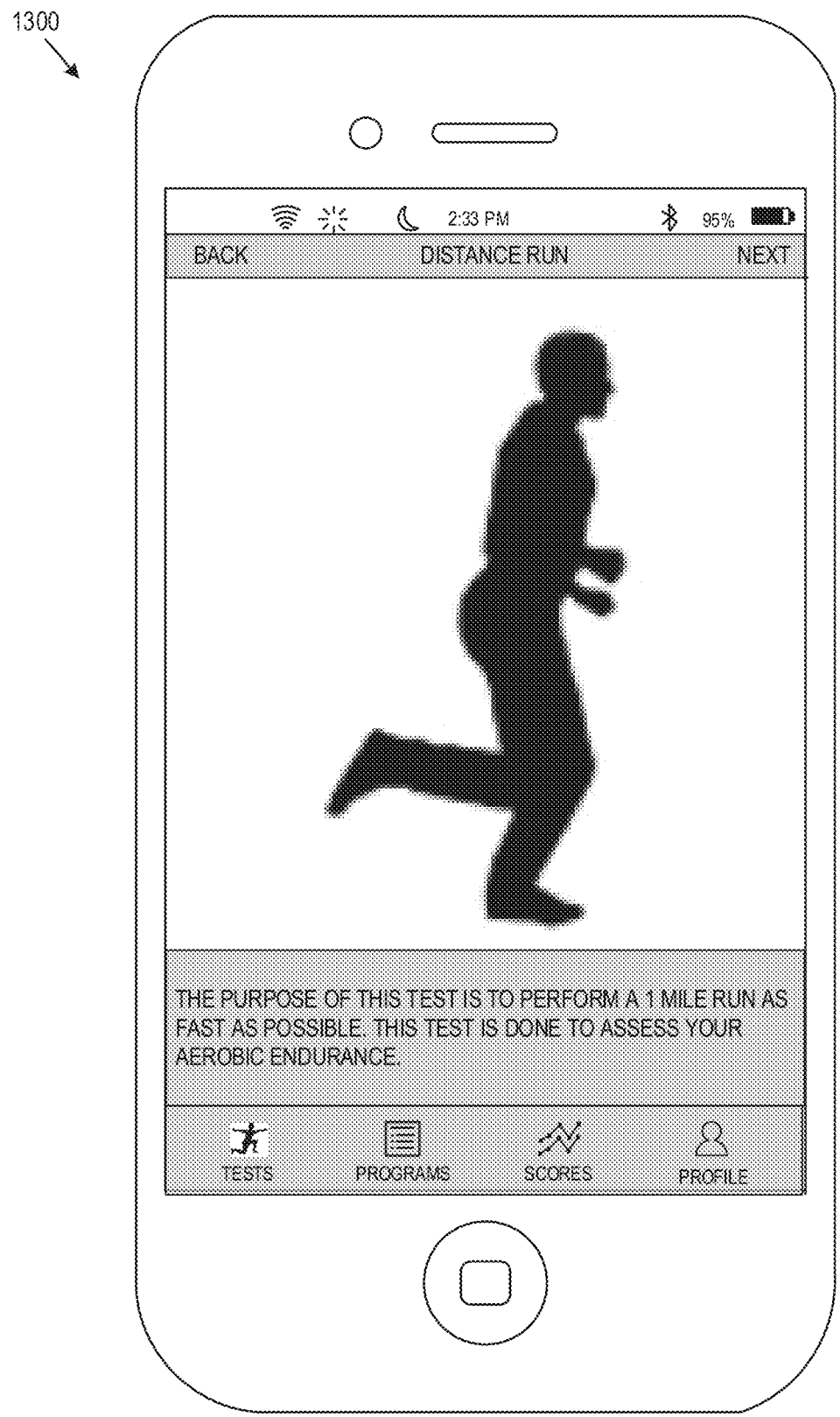
FIG. 13 shows an example of a user interface displaying an indication of a normalization activity to the user on the user device.

Referring now to FIG. 13, shown therein is an example of a user interface 1300 displayed on a user device such as user device 102. User interface 1300 is an example of a user interface displaying an indication of a normalization activity that has been determined for the user. The user interface 1300 also identifies that the particular normalization activity selected may be used to normalize the user's fitness across a particular fitness category. In the example shown in user interface 1300, the normalization activity determined for the user is a distance run with an activity level of 1 mile in length. Various other activity levels for distance runs may be determined, e.g. 3 kilometers, 5 kilometers, 10 kilometers etc. User interface 1300 also indicates that the particular normalization activity can be used to assess the user's fitness in an aerobic endurance fitness category.

Figure 14:
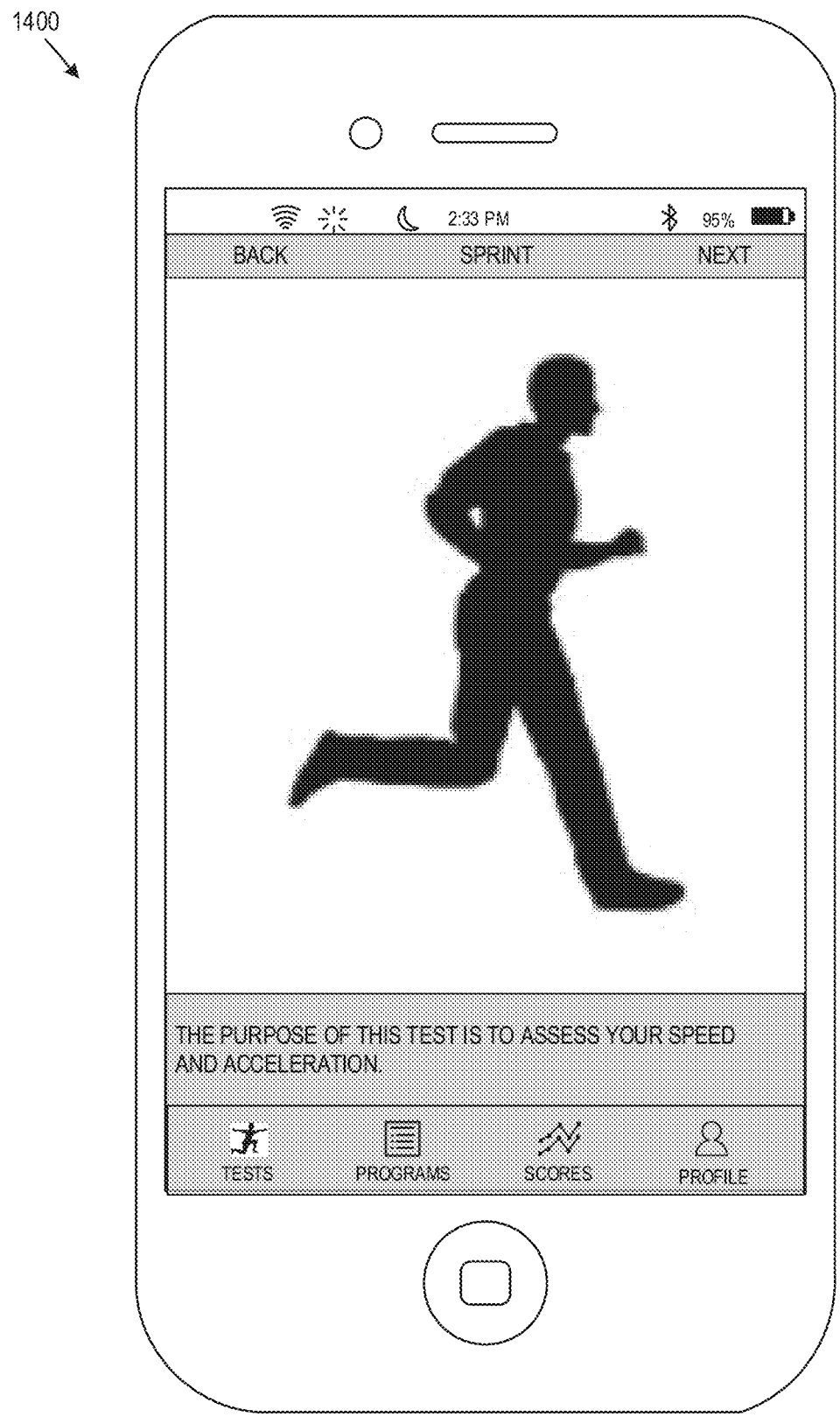
FIG. 14 shows another example of a user interface displaying an indication of a normalization activity to the user on the user device.

Referring now to FIG. 14, shown therein is another example of a user interface 1400 displayed on a user device such as user device 102. In user interface 1400, the normalization activity determined is a 40-yard dash. In some cases, a single normalization activity may be used to assess a user's fitness in multiple fitness categories. As user interface 1400 indicates, the 40-yard dash normalization activity may be used to assess the user's fitness in two fitness categories, namely speed and acceleration. In some cases, activity results from multiple normalization activities can be used in combination to assess a user's fitness in one or more fitness categories.

Figure 15:
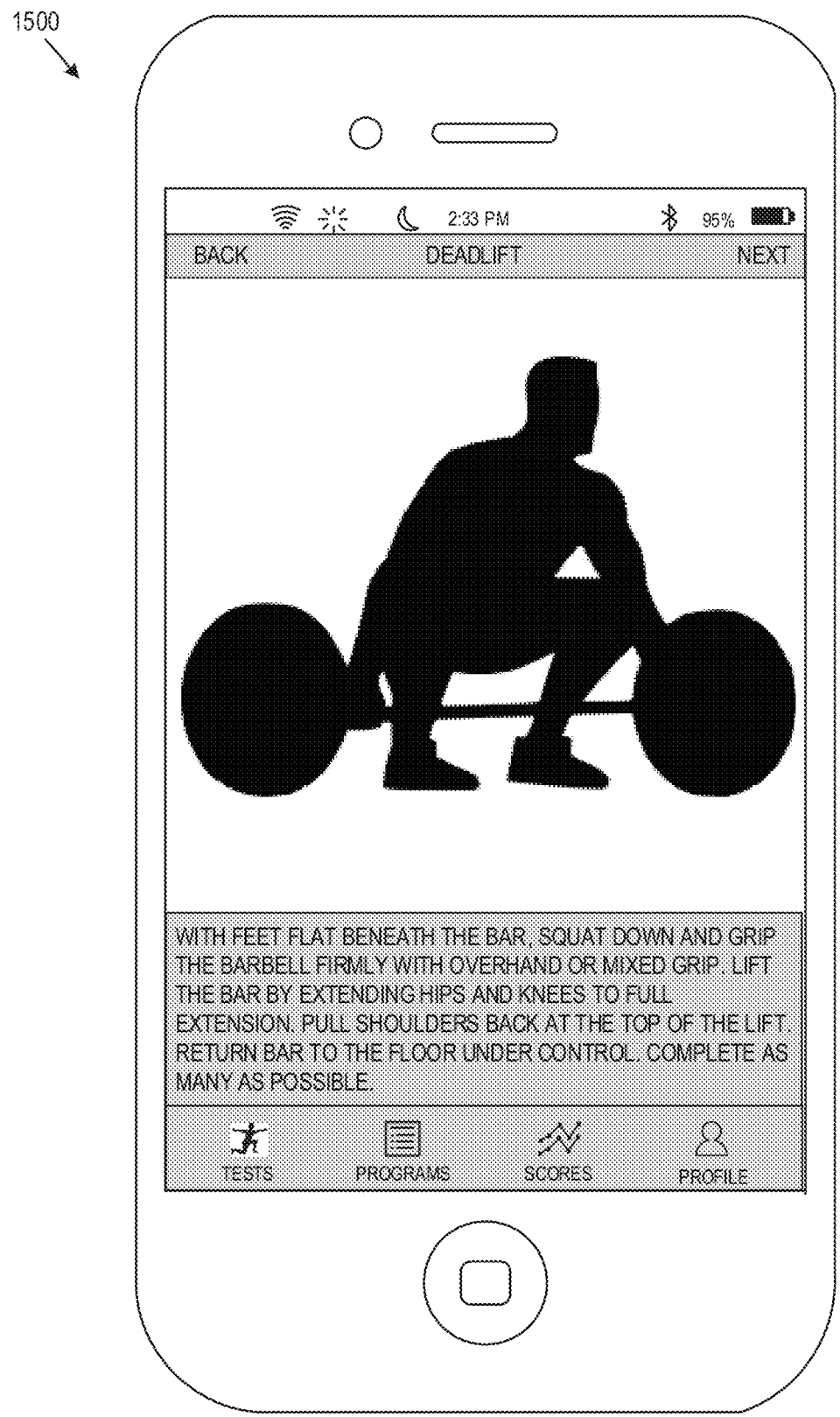
FIG. 15 shows a further example of a user interface displaying an indication of a normalization activity to the user on the user device.

Referring now to FIG. 15, shown therein is a further example of a user interface 1500 displayed on a user device such as user device 102. In user interface 1500, the normalization activity being indicated is a deadlift. As user interface 1500 indicates, the fitness normalization system may provide instruction to a user to properly perform a normalization activity. This may assist the user in completing the activity, as well as attempt to minimize variation in how different users perform the same normalization activity.

Figure 16:
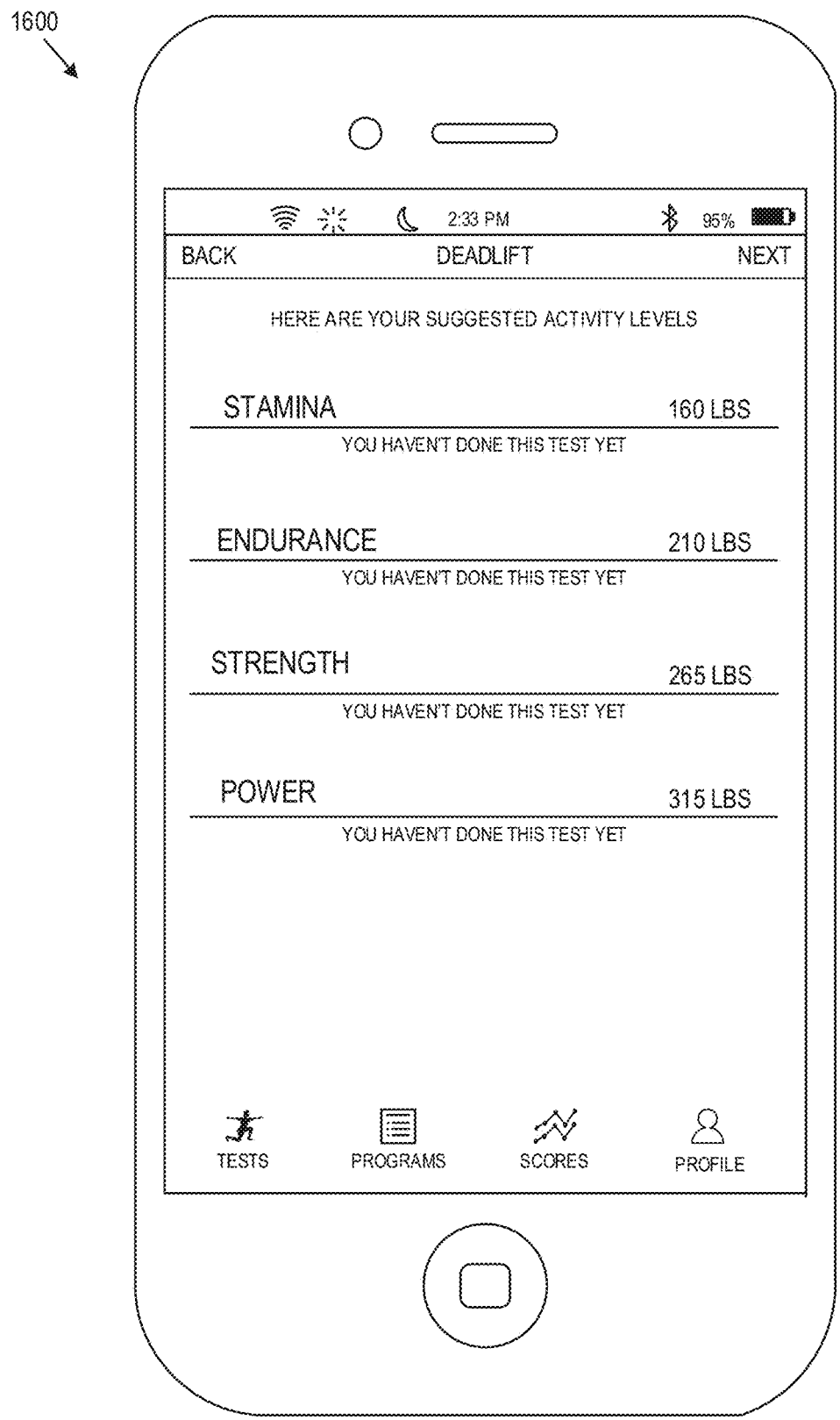
FIG. 16 shows an example of a user interface displaying an indication of multiple activity levels for the normalization activity of FIG. 15 to the user on the user device.

Referring now to FIG. 16, shown therein is an example of a user interface 1600 displayed on a user device such as user device 102. User interface 1600 indicates that the normalization activity displayed may be performed at 4 different activity levels. In the example shown in user interface 1600, each activity level may be determined for the purpose of assessing the user in a different fitness category. In some cases, the activity levels may also include modifications to the normalization activity. Such modifications may be displayed to on the user device to indicate to the user how to perform the normalization activity for that activity level.

As mentioned above, the activity level(s) may be determined for a user based on body weight data included in the normalization base data for the user. For example, the activity levels may be selected as a function or percentage of body weight. This may minimize variation in activity results among users for activities where the user's body weight may positively or negatively affect their performance of the normalization activity.

In the example shown in FIG. 9 the user had a body weight of 210 lbs. In this case, the fitness normalization system has selected a first activity level of 160 lbs, or ~75% of the user's body weight, for the deadlift normalization activity. Activity results gathered of the user performing the deadlift at the first activity level may also be used to assess the user in the stamina fitness category.

Similarly, the second activity level of 210 lbs or 100% of the user's body weight may be used to assess the user's endurance. The third activity level of 265 lbs or 125% of the user's body weight may be used to assess the user's strength, and the fourth activity level of 315 or 150% of the user's body weight may be used to assess the user's power.

Figure 17:
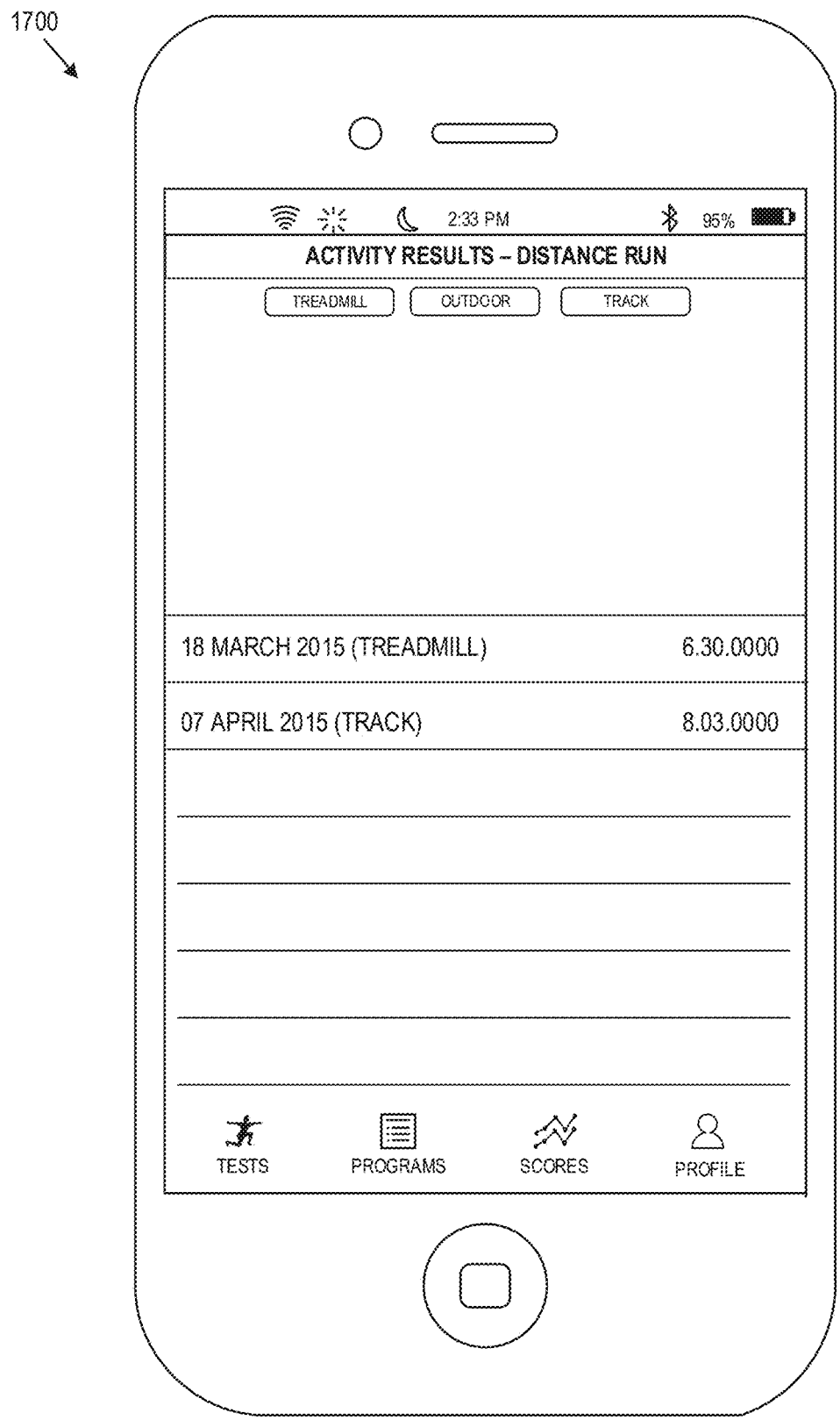
FIG. 17 shows an example of a user interface displaying activity results to the user on the user device.

Referring now to FIG. 17, shown therein is an example of a user interface 1700 displayed on a user device such as user device 102. User interface 1700 shows activity results received from the user for a mile run normalization activity on two different occasions. The activity results may also include some environmental indicators that indicate the environment in which the activity result was attained. For example, user interface 1700 shows that the mile run was completed at a much faster pace on a treadmill than on a track. User interface 1700 may allow a user to review past activity results, and determine if positive progress is being made in their activity results.

Referring now to FIG. 18, shown therein is an example of a user interface 1800 displayed on a user device such as user device 102. User interface 1800 shows normalized activity results corresponding to the activity results of FIG. 17. The user whose results are shown in FIG. 17 corresponds to a user having normalization base data of a moderate level of activity, with a general fitness regime. The normalized activity results shown in user interface 1800 were generated using a comparator population having a comparator range of users having normalization base data with a vigorous level of activity and a distance runner fitness regime.

Referring now to FIG. 19, shown therein is an example of a user interface 1900 displayed on a user device such as user device 102. User interface 1900 of a target fitness regime being displayed to the user. The target fitness regime shown in user interface 1900 provides some guidance to the user to improve their performance in a mile run normalization activity. The system 106 has set a target fitness regime with a three week duration for the user.

At the end of the target regime duration, the user may perform the normalization activity again to assess whether the user's activity results for that normalization activity have progressed. The user device 102 may also monitor activity results during the target fitness regime, and when the user's activity results are being collected. These activity results can be used to update the normalization base data for the user. For instance, if the user adheres to the target fitness regime, the user device 102 or server 106 may determine that the user's activity level has increased. The user's normalization base data can be automatically updated, and the normalization factors for the user may be adjusted accordingly if the same comparator population is being used.

In some embodiments, the systems and methods for normalizing activity results described herein can also be applied to identify potential fitness regimes for a user. A user may provide normalization base data and at least one activity result. The user may also identify at least one desired activity result corresponding to the activity results provided. For example, the user may identify the desired activity results as results they hope to achieve. Using the normalization factors determined for the plurality of user populations and comparator populations, the system 100 may identify one or more comparator populations that closely correlate to the desired activity results based on the user's normalization base data and the received activity results. In effect, the desired activity results correspond to normalized activity results that would be determined for the user based on the identified comparator populations.

The system 100 may display the identified comparator populations to the user. For example, the identified comparator populations may identify for the user a potential fitness regime that they should follow for a defined period of time in order to achieve the desired activity results. In some cases, the users may also identify specific normalization dimensions of the comparator range that may differ from the user's normalization base data. For example, the user may specify that they do not want to increase the frequency of activity, but the activity types and exertion level may be different. The system 100 may identify comparator populations that may allow the user to achieve the desired results.

The present invention has been described here by way of example only. Various modification and variations may be made to these exemplary embodiments without departing from the spirit and scope of the invention, which is limited only by the appended claims.

We claim:

1. A method of generating normalized activity results using a server that is in communication with a plurality of computing devices associated with a plurality of users, each computing device having a processor and a non-transitory memory, the method comprising:

providing a normalization application on a first computing device of the plurality of computing devices, wherein the normalization application comprises computer-executable instructions usable to configure the processor of the first computing device;

receiving by the normalization application operating on the first computing device, normalization base data for a first user associated with the first computing device, wherein the normalization base data for the first user comprises user base data for at least one normalization dimension, wherein the normalization base data defines characteristics of the first user;

assigning by the processor of the first computing device as configured by the normalization application operating on the first computing device, the first user to a first user population based on the received normalization base data for the first user, the first user population being defined to include users having normalization base data within a first user population range for each of the at least one normalization dimensions;

determining an average first user population activity result based on activity results received by the server from a plurality of population users in the first user population for at least one specific normalization activity;

determining a comparator population for the first user, the comparator population being defined to include users having normalization base data within a comparator range for each of the at least one normalization dimensions, wherein for at least one of the normalization dimensions the comparator range is different from the first user population range and the first user population range and the comparator population range do not overlap;

determining an average comparator population activity result based on activity results received by the server from a plurality of comparator users in the comparator population for the at least one specific normalization activity;

receiving by the normalization application operating on the first computing device at least one first activity result for the first user, wherein the at least one first activity result corresponds to the at least one specific normalization activity, wherein the at least one first activity result is received from at least one sensor in communication with the normalization application operating on the first computing device, wherein the at least one sensor is operable to monitor the first user's movements while performing the at least one specific normalization activity;

determining by the normalization application operating on the first computing device, at least one activity-specific normalization factor for the first user based on the average comparator population activity result determined for the comparator users in the comparator population, and the average user population activity result determined by the server from the population users in the first user population;

generating by the processor of the first computing device, as configured by the normalization application, normalized activity results for the first user by adjusting the at least one first activity result, using the corresponding at least one activity-specific normalization factor, wherein the normalized activity results define adjusted results for the at least one specific normalization activity; and displaying by the processor of the first computing device, as configured by the normalized application, the normalized activity results at the first computing device.

2. The method of claim 1, further comprising:
monitoring activity results from the first user collected over time using the normalization application operating on the first computing device;
updating the normalization base data for the first user based on the monitored activity results; and
removing the first user from first user population to which the first user was assigned and re-assigning the first user to a different user population based on the updated normalization base data.

3. The method of claim 1, further comprising:
determining a suggested fitness regime for the first user based on the normalization base data for the first user and the at least one activity result; and
displaying the suggested fitness regime through the normalization application operating on the first computing device.

4. The method of claim 3, further comprising:
determining the suggested fitness regime by:
receiving, by the normalization application operating on the first computing device, at least one desired activity result for the first user;
identifying at least one potential comparator population based on the at least one desired activity result for the first user, wherein each potential comparator population is identified as having average comparator population activity results that correspond to the at least one desired activity result;
determining at least one potential fitness regime based on the at least one potential comparator population, wherein for each potential comparator population the at least one normalization dimension for the comparator normalization base data for that potential comparator population comprises a fitness normalization dimension that corresponds to a potential fitness regime associated with that potential comparator population; and
selecting the suggested fitness regime as a particular potential fitness regime from the least one potential fitness regime.

5. The method of claim 4, wherein
for each potential comparator population, the comparator normalization base data comprises comparator user demographic data for a demographic normalization dimension;
the normalization base data for the first user comprises first user demographic data for the demographic normalization dimension; and
the particular potential fitness regime is selected by:
identifying a selected comparator population as the potential comparator population having comparator user demographic data that corresponds to the first user demographic data; and
selecting the particular potential fitness regime as the potential fitness regime associated with the selected comparator population.

6. The method of claim 1, wherein:
the comparator population is determined to include users having normalization base data within a particular comparator range, wherein the particular comparator range is defined to correspond to a specific sport; and
the normalized activity results displayed at the first computing device correspond to athletic performance in the specific sport for the first user.

7. The method of claim 3, wherein:
the normalization base data for the first user comprises fitness regime data indicating a current fitness regime for the first user; and
the comparator population for the first user is defined to include users having fitness regime data that corresponds to the suggested fitness regime whereby that the normalized activity results are normalized based on average activity results from users associated with the suggested fitness regime.

8. The method of claim 2, wherein the at least one sensor comprises an activity tracking sensor provided by an activity tracking device in communication with the first computing device.

9. The method of claim 2, wherein the normalization application is provided through a web page over the Internet, and the first computing device operates the normalization application by accessing the web page.

10. A system for generating normalized activity results for a first user, the system comprising:
a plurality of computing devices associated with a plurality of users, wherein a first computing device from the plurality of computing devices is associated with the first user, and wherein each computing device of the plurality of computing devices has a processor, a non-transitory memory and a normalization application operating thereon, the normalization application comprises computer-executable instructions usable to configure the processor of the corresponding computing device;
a server in communication with the plurality of computing devices, the server configured to provide the normalization application to each of the plurality of computing devices;
wherein:
the first computing device is configured by the normalization application to receive normalization base data for the first user, wherein the normalization base data for the first user comprises user base data for at least one normalization dimension, wherein the normalization base data defines characteristics of the first user;
the processor of the first computing device is configured by the normalization application to assign the first user to a first user population based on the received normalization base data, the first user population being defined to include users having normalization base data within a first user population range for each of the at least one normalization dimensions;

the first computing device is configured by the normalization application to determine a comparator population for the first user, the comparator population being defined to include users having normalization base data within a comparator range for each of the at least one normalization dimensions, wherein for at least one of the normalization dimensions the comparator range is different from the first user population range and the first user population range and the comparator population range do not overlap;

the server is further configured to:

collect, using the normalization application operating on at least some of the plurality of computing devices, comparator population activity results for at least one specific normalization activity performed from a plurality of comparator users in the comparator population;

determine an average comparator population activity result based on activity results received by the server from a plurality of comparator users in the comparator population for the at least one specific normalization activity;

collect, using the normalization application operating on at least some of the plurality of computing devices, user population activity results for at least one specific normalization activity from a plurality of population users in the first user population;

determine an average first user population activity result based on activity results received by the server from a plurality of population users in the first user population for at least one specific normalization activity;

define at least one activity-specific normalization factor for the comparator population and the user population using the average comparator population activity result and the average user population activity result;

the first computing device is further configured by the normalization application to determine the at least one activity-specific normalization factor for the first user based on the comparator population and the normalization base data received for the first user; and the processor of the first computing device is further configured by the normalization application to:

receive at least one first activity result for the first user, wherein the at least one first activity result corresponds to the at least one specific normalization activity, wherein the at least one first activity result is received from at least one sensor in communication with the normalization application operating on the first computing device, wherein the at least one sensor is operable to monitor the first user's movements while performing the at least one specific normalization activity;

generate normalized activity results for the first user by adjusting the at least one first activity result, using the corresponding at least one activity-specific normalization factor, wherein the normalized activity results define adjusted results for the at least one specific normalization activity; and display the normalized activity results at the first computing device.

11. The system of claim 10, wherein the server is further configured to monitor activity results from the first user collected over time using the normalization application operating on the first computing device; and the processor of the first computing device is further configured by the normalization application to:

update the normalization base data for the first user based on the monitored activity results; and remove the first user from first user population to which the first user was assigned and re-assigning the first user to a different user population based on the updated normalization base data.

12. The system of claim 10, wherein the processor of the first computing device is further configured by the normalization application to:

determine a suggested fitness regime for the first user based on the normalization base data for the first user and the at least one activity result; and display the suggested fitness regime.

13. The system of claim 12, wherein the processor of the first computing device is further configured by the normalization application to:

determine the suggested fitness regime by:

receiving at least one desired activity result for the first user;

identifying at least one potential comparator population based on the at least one desired activity result for the first user, wherein each potential comparator population is identified as having average comparator population activity results that correspond to the at least one desired activity result;

determining at least one potential fitness regime based on the at least one potential comparator population, wherein for each potential comparator population the at least one normalization dimension for the comparator normalization base data for that potential comparator population comprises a fitness normalization dimension that corresponds to a potential fitness regime associated with that potential comparator population; and selecting the suggested fitness regime as a particular potential fitness regime from the least one potential fitness regime.

14. The system of claim 13, wherein for each potential comparator population, the comparator normalization base data comprises comparator user demographic data for a demographic normalization dimension;

the normalization base data for the first user comprises first user demographic data for the demographic normalization dimension; and the processor of the first computing device is further configured by the normalization application to select the particular potential fitness regime by:

identifying a selected comparator population as the potential comparator population having comparator user demographic data that corresponds to the first user demographic data; and selecting the particular potential fitness regime as the potential fitness regime associated with the selected comparator population.

15. The system of claim 10, wherein the processor of the first computing device is further configured by the normalization application to:

determine the comparator population to include users having normalization base data within a particular comparator range, wherein the particular comparator range is defined to correspond to a specific sport; and wherein the normalized activity results displayed at the first computing device correspond to athletic performance in the specific sport for the first user.

16. The system of claim 12, wherein:

the normalization base data for the first user comprises fitness regime data indicating a current fitness regime for the first user; and the comparator population for the first user is defined to include users having fitness regime data that corresponds to the suggested fitness regime whereby that the normalized activity results are normalized based on average activity results from users associated with the suggested fitness regime.

17. The system of claim 11 further comprising an activity tracking device in communication with the first computing device, wherein the at least one sensor comprises an activity tracking sensor provided by the activity tracking device.

18. The system of claim 11, wherein the server is configured to provide the normalization application through a web page over the Internet, and the first computing device is configured to operate the normalization application by accessing the web page.

19. A non-transitory, computer-readable storage medium storing instructions executable by a processor coupled to the storage medium, the instructions for programming the processor to perform a method of generating normalized activity results through communication with a server that is in communication with a plurality of computing devices associated with a plurality of users, wherein the instructions are executable to configure the processor to:

receive normalization base data for a user, wherein the normalization base data for the user comprises user base data for at least one normalization dimension, wherein the normalization base data defines characteristics of the user;

assign the user to a user population based on the received normalization base data for the user, the user population being defined to include users having normalization base data within a user population range for each of the at least one normalization dimensions;

determine an average user population activity result based on activity results received by the server from a plurality of population users in the user population for at least one specific normalization activity;

determine a comparator population for the user, the comparator population being defined to include users having normalization base data within a comparator range for each of the at least one normalization dimensions, wherein for at least one of the normalization dimensions the comparator range is different from the user population range and the user population range and the comparator population range do not overlap;

determine an average comparator population activity result based on activity results received by the server from a plurality of comparator users in the comparator population for the at least one specific normalization activity;

receive at least one activity result for the user, wherein the at least one activity result corresponds to the at least one specific normalization activity, wherein the at least one activity result is received from at least one sensor in communication with the processor, wherein the at least one sensor is operable to monitor the user's movements while performing the at least one specific normalization activity;

determine at least one activity-specific normalization factor for the user based on the average comparator population activity result determined for the comparator users in the comparator population, and the average user population activity result determined by the server from the population users in the user population;

generate normalized activity results for the user by adjusting the at least one activity result, using the corresponding at least one activity-specific normalization factor, wherein the normalized activity results define adjusted results for the at least one specific normalization activity; and display the normalized activity results.

* * * * *